(12) United States Patent
Hu et al.

(10) Patent No.: US 10,159,912 B2
(45) Date of Patent: Dec. 25, 2018

(54) METHODS OF EXTRACTING PHOSPHORUS FROM DISTILLATES

(71) Applicant: REGENTS OF THE UNIVERSITY OF MINNESOTA, Minneapolis, MN (US)

(72) Inventors: Bo Hu, Inver Grove Heights, MN (US); Qiyang He, Nanjing (CN)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/148,454

(22) Filed: May 6, 2016

(65) Prior Publication Data

US 2016/0325205 A1 Nov. 10, 2016

Related U.S. Application Data

(60) Provisional application No. 62/157,676, filed on May 6, 2015.

(51) Int. Cl.
| | |
|---|---|
| *B01D 15/36* | (2006.01) |
| *B01J 41/12* | (2017.01) |
| *C07C 29/76* | (2006.01) |
| *B01D 15/20* | (2006.01) |
| *C07F 9/117* | (2006.01) |
| *C12F 3/00* | (2006.01) |
| *C12F 3/10* | (2006.01) |
| *B01J 49/07* | (2017.01) |
| *B01J 49/57* | (2017.01) |

(52) U.S. Cl.
CPC ......... *B01D 15/363* (2013.01); *B01D 15/203* (2013.01); *B01J 41/12* (2013.01); *B01J 49/07* (2017.01); *B01J 49/57* (2017.01); *C07C 29/76* (2013.01); *C07F 9/117* (2013.01); *C12F 3/00* (2013.01); *C12F 3/10* (2013.01)

(58) Field of Classification Search
CPC .................................................. B01D 15/363
See application file for complete search history.

(56) References Cited

U.S. PATENT DOCUMENTS 7,709,676 B2 * 5/2010 Kanou ................... C07C 253/34
558/443
2014/0017750 A1 1/2014 Solbak et al.

OTHER PUBLICATIONS

Alkan-Ozkaynak, "Phosphorus flow and characterization in dry-grind corn ethanol plants" Feb. 2012 *J. Environ. Qual.* 41:1695-1701.
Angel, "Phytic acid chemistry: influence on phytin-phosphorus availability and phytase efficacy" 2002 *J. Appl. Poult. Res.* 11:471-580.
Batal, "Mineral composition of distillers dried grains with solubles" 2003 J. Appl. Poultry Res. 12, 400-403.
Belyea, "Element concentrations of dry-grind corn-processing streams" Aug. 2006 Appl. Biochem. Biotechnol. 134(2):113-128.
Bhadra, "Characterization of chemical and physical properties of distiller's dried grain with solubles (DDGS) for value added uses" 2007 ASAE Paper 077009. ASABE, Minneapolis, MN.
Boisen, "Prediction of the total tract digestibility of energy in feedstuffs and pig diets by in vitro analyses" Oct. 1997 *Animal Feed Science and Technology*, 68(3-4):277-286.
Canan, "Studies on the extraction and purification of phytic acid from rice bran" Nov. 2011 *Journal of Food Composition and Analysis*, 24(7)1057-1063.
Celi, Interaction of inositol hexaphosphate on clays: Adsorption and charging phenomena. Aug. 1999 *Soil Sci.* 164(8):574-585.
Chen, "Corn seeds as bioreactors for the production of phytase in the feed industry" May 2013 *Journal of Biotechnology* 165(2):120-126.
Cromwell, "Efficacy of low activity, microbeal phytase in improving the bioavailability of phosphorous in corn-soybean meal diets for pigs" Dec. 1995 *J. Anim. Sci.* 73:449-458.
Cupisti, "Management of Natural and Added Dietary Phosphorus Burden in Kidney Disease" Mar. 2013 *Seminars in Nephrology* 33(2):180-190.
Ganasan, "Calcium phosphate nanoparticles as nuclei for the preparation of colloidal calcium phytate" Jun. 2008 New J. Chem., 32:1326-1330.
Groot, "Multiphasic analysis of gas production kinetics for in vitro fermentation of ruminant feeds" Feb. 1996 *Animal Feed Science and Technology*, 64(1):77-89.
He, "Preparation and FT-IR Characterization of Metal Phytate Compounds" Jul. 2006 *J. Environ. Qual.* 35(4):1319-1328.
He, "Phytate extraction from co-products of the corn ethanol" 2014 AIChE Annual Meeting, Presentation Nov. 18, 2014.
Kaufman, "The effect of pH on the adsorption properties of the phytate molecule" Oct. 1970 *Archs Oral Biol.* 15(10):917-934.
Kerley, "Alkaline Hydrogen-Peroxide Treatment Unlocks Energy in Agricultural By-Products" 1985 *Science*, 230(4727): p. 820-822.
Khullar, "Use of Phytases in Ethanol Production from E-Mill Corn Processing" May 2011 *Cereal Chem.* 88(3):223-227.
Koelsch, "Nutrient balance on Nebraska livestock confinement systems" Jan. 1999 *J. Anim. Sci.* 77:63-71.
Lee, "Dietary phytic acid lowers the blood glucose level in diabetic KK mice" Sep. 2006 *Nutrition Research* 26(9):474-479.
Lehrfeld, "High-performance liquid chromatography analysis of phytic acid on a pH-stable, macroporous polymer column" 1989 *Cereal Chem.* 66(6):510-515.
Letourneau-Montminy, "Modeling the fate of dietary phosphorus in the digestive tract of growing pigs" 2011 *J. Animal Science*, 89(11):3596-3611.
Liu, "Changes in mineral concentrations and phosphorus profile during dry-processing of corn into ethanol" Feb. 2011 *Bioresour. Technol.* 102(3):3110-3118.

(Continued)

*Primary Examiner* — Shawquia Jackson
(74) *Attorney, Agent, or Firm* — Mueting, Raasch & Gebhardt, PA

(57) ABSTRACT

Methods of processing distillates, methods of removing at least some portion of total phosphorus in a distillate, methods of removing at least some portion of the soluble inorganic phosphorus, phytate phosphorus, or some combination thereof in a distillate, methods for obtaining phytate from distillates, methods for producing phytate derivatives and combinations thereof.

8 Claims, 16 Drawing Sheets

(56) References Cited

OTHER PUBLICATIONS

Lott, "Phytic acid and phosphorus in crop seeds and fruits: a global estimate" Mar. 2000 *Seed Science Research*, 10(1):11-33.

March, "Determination of phytic acid by gas chromatography-mass spectroscopy: application to biological samples" Jun. 2001 *J. of Chromatography B.* 757(2):247-255.

Minihane, "Iron absorption and the iron binding and anti-oxidant properties of phytic acid" Sep. 2002 *International Journal of Food Science and Technology* 37(7):741-748.

Noureddini, "Degradation of Phytates in Distillers' Grains and Corn Gluten Feed by *Aspergillus niger* Phytase" Oct. 2009 *Appl. Biochem. Biotechnol.* 159(1): 11-23.

Noureddini, "Distribution of phosphorus compounds in corn processing" Jan. 2009 *Bioresour. Technol.* 100(2):731-736.

Noureddini, "An integrated approach to the degradation of phytates in the corn wet milling process" Dec. 2010 *Bioresour. Technol.* 101(23):9106-9113.

Park, "Determination of the phytic acid levels in infant foods using different analytical methods" Sep. 2006 *Food Control* 17(9):727-732.

Phillippy, "Preparation of inositol phosphates from sodium phytate by enzymatic and nonenzymatic hydrolysis" Apr. 1987 *Anal. Biochem.* 162(1): 115-121.

Rausch. Proc Intl. Starch Technol. Conf. In: Rausch KD, Singh V, Tumbleson ME, editors. Coproduct streams from dry grind corn processing. Urbana, IL: University of Illinois at Urbana-Champaign; 2005.

Rausch, "The future of co-products from corn processing" Jan. 2006 *Appl. Biochem. Biotechnol.* 128(1):47-86.

Ravindran, "Phytin: Occurrence, bioavailability and implications in poultry nutrition" 1995 *Poult. Avian Biol.* 6:125-143.

Reddy, "Phytates in legumes and cereals" 1982 *Adv. in Food Res.* 28:1-92.

RFA, "Ethanol Industry Outlook" 2012 <http://www.ethanolrfa.org/news/entry/2012-ethanol-industry-outlook-and-pocket-guide-to-ethanol-now-available>.

RFA, "Annual Industry Outlook" 2013 <http://www.ethanolrfa.org/pages/annual-industry-outlook>.

Saw, "Effects of inositol hexaphosphate (Phytate) on calcium binding, calcium oxalate crystallization and in vitro stone growth" Jun. 2007 "The Journal of Urology" 177(6):2366-2370.

Spiehs, "Nutrient database for distiller's dried grains with solubles produced from new ethanol plants in Minnesota and South Dakota" 2002 *J. Anim. Sci.* 80:2639-2645.

Sun, "Enrichment and antioxidant properties of flavone C-glycosides from trollflowers using macroporous resin" Nov. 2013 *Food Chemistry*, 141(1):533-541.

Tahir, "Phytate and other nutrient components of feed ingredients for poultry." Apr. 2012 *Poultry Science* 91(4):928-935.

Vucenik, "Protection against cancer by dietary IP6 and inositol" 2006 *Nutrition and Cancer* 55(2):109-125.

Walk, "Influence of diet, phytase, and incubation time on calcium and phosphorus solubility in the gastric and small intestinal phase of an in vitro digestion assay" Sep. 2012 *Journal of Animal Science*, 90(9): p. 3120-3125.

Woyengo, "Review: Anti-nutritional effects of phytic acid in diets for pigs and poultry—current knowledge and directions for future research" Mar. 2013 *Canadian Journal of Animal Science*, 93(1):9-21.

Xu, "Neuroprotective effect of the natural iron chelator, phytic acid in a cell culture model of Parkinson's disease" Mar. 2008 *Toxicology* 245(1-20):101-108.

Zhao, "Separation of tungsten and molybdenum using macroporous resin: Equilibrium adsorption for single and binary systems" Nov. 2013 *Hydrometallurgy* 140, 120-127.

\* cited by examiner

METHODS OF EXTRACTING PHOSPHORUS FROM DISTILLATES

CROSS-REFERENCE TO RELATED APPLICATION

This application claims priority to U.S. Provisional Patent Application Ser. No. 62/157,676 filed May 6, 2015, entitled METHODS OF EXTRACTING PHYTATE FROM DISTILLATES the disclosure of which is incorporated by reference herein in its entirety.

SUMMARY

Disclosed herein are methods of processing distillates, methods of removing at least some portion of total phosphorus in a distillate, methods of removing at least some portion of the soluble inorganic phosphorus, phytate phosphorus, or some combination thereof in a distillate, methods for obtaining phytate from distillates, methods for producing phytate derivatives and combinations thereof.

Also disclosed are methods for processing a distillate, the methods include contacting the distillate with an anion exchange resin, wherein the distillate includes total phosphorus, wherein total phosphorus includes soluble inorganic phosphorus, phytate phosphorus, other forms of phosphorus, or combinations thereof and wherein at least some of the soluble inorganic phosphorus, phytate phosphorus or both in the distillate is adsorbed on the anion exchange resin; and separating at least some of the distillate from the anion exchange resin to form a modified distillate, wherein the modified distillate has less total phosphorus than the distillate.

Also disclosed are methods for removing phytate from a distillate, the methods include contacting the distillate with an anion exchange resin, wherein the distillate includes phytate phosphorus and wherein at least some of the phytate phosphorus in the distillate is adsorbed on the anion exchange resin; and desorbing at least some of the adsorbed phytate phosphorus from the anion exchange resin to obtain a phytate solution, wherein the phytate solution includes phytate.

Further disclosed are methods for processing a distillate, the methods include contacting the distillate with an anion exchange resin, wherein the distillate includes soluble inorganic phosphorus, phytate phosphorus, or combinations thereof and wherein at least some of the soluble inorganic phosphorus, phytate phosphorus or both in the distillate is adsorbed on the anion exchange resin; separating at least some of the distillate from the anion exchange resin to form a modified distillate, wherein the modified distillate has less soluble inorganic phosphorus, phytate phosphorus, or combinations thereof than the distillate; desorbing at least some of the soluble inorganic phosphorus, phytate phosphorus, or combinations thereof from the anion exchange resin; and regenerating the anion exchange resin.

These and various other features and advantages will be apparent from reading the following detailed description.

BRIEF DESCRIPTION OF THE FIGURES

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
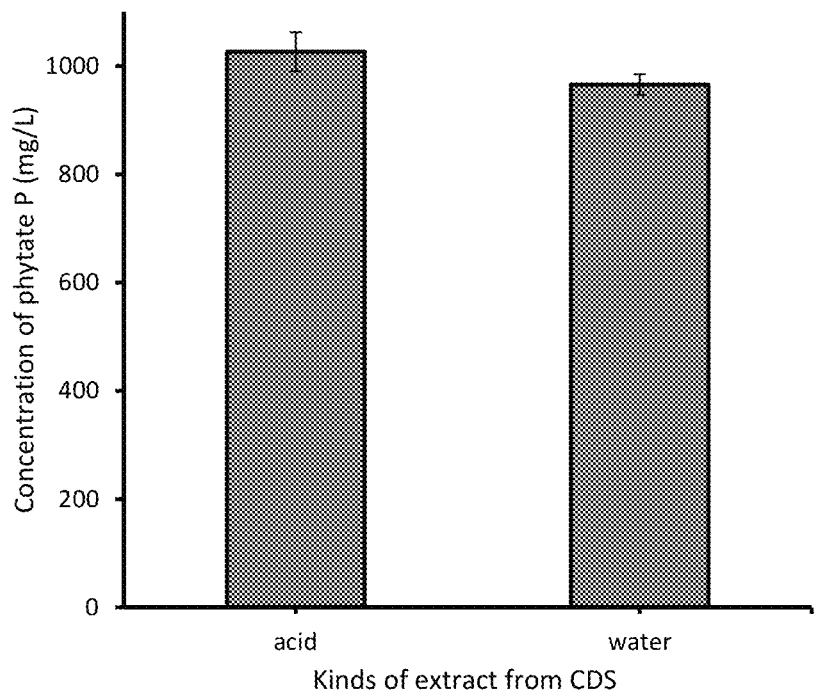
FIG. 1 shows the concentration of phosphorus from phytate in 1 M HCl and water extract of condensed distillers solubles (CDS).

Ethanol and various other products produced from corn have become more and more valuable. Dry milling processes, the major industrial method for the production of corn ethanol is utilized to produce roughly 80% of corn ethanol. In dry milling processes, whole stillage (WS) is a byproduct of the fermentation of corn to ethanol. After centrifugation of WS, thin stillage (TS) can be separated from wet distillers grains (WDG). Condensed distillers solubles (CDS) is produced from evaporation of TS. Drying the blend of WDG and CDS generates distillers dried grains with solubles (DDGS) which is the major commercial co-product of the corn ethanol industry. In recent years, as the application of dry grind processes has extended into the corn ethanol industry, production of DDGS has dramatically increased.

The presence of large amounts of important nutrients (fat, fiber, protein and unconverted starch) in DDGS have resulted in relatively wide use of DDGS as animal feed in the livestock industry; 79% of DDGS was fed to ruminant animals (beef and dairy), and 20% was fed to nonruminant animals (poultry and swine) in 2013. DDGS also contains a wide variety of minerals, such as potassium, magnesium, zinc, sulfur and phosphorous (P). Phosphorus is the third most expensive nutrient in animal feeds, and is present at levels of 5 to 10 g P/kg (dry basis) in DDGS, which is much higher than the requirements of most ruminant animals.

Phytate, the salt form of phytic acid (PA), is also called inositol hexaphosphate (IP6). Phytate is the major storage form of phosphorus in corn. 50 to 80% of phosphorus in corn exists as phytate. As yeast secretes phytase during the fermentation process in ethanol production, a portion of the phytate is degraded to inositol mono-, bis-, tris-, tetra-, and pentakisphosphates (IP1, IP2, IP3, IP4, and IP5, respectively) and inorganic phosphorus. Studies have shown that 40-50% of the phosphorus remaining in DDGS is still in the phytate form.

For nonruminant animals, the phosphorus in phytate cannot be directly assimilated. Because of the excess levels and/or inability to assimilate, excess phosphorus can therefore be deposited in animal waste, which may potentially result in high levels of phosphorus in runoff water and concomitant eutrophication in surface and underground water bodies.

The remaining phytate in DDGS acts as a powerful chelator in animals where DDGS is included as part of their diet so that the bioavailability of minerals and proteins is diminished by binding with phytate. Phytase is often added during the dry milling process to remove some of the phytate before the ethanol fermentation. Phytase is also often added in feed products before they are fed to animals to avoid phytate digestion issues. Adding phytase will increase the nutrient availability of DDGS to the animals Phytate is a good chelator, an anti-oxidant, a food preservative, and the raw material to produce myo-inositol (vitamin B8). These functions make it widely used in a variety of commercial applications including but not limited to foods, textiles, daily use chemicals and the plastic industries. In recent years, the beneficial effects of phytate have been highlighted in the prevention of human disease, especially for renal calculi, diabetes, cancer and Parkinson's disease. Therefore, if phytate can be extracted from distillates, specifically from DDGS, it would not only reduce phosphorus pollution in water bodies and enhance the feeding and economic value of DDGS, but would also bring extra revenue to the corn ethanol industry by generating higher value products.

Soluble inorganic phosphorus, a component of total phosphorus in compositions used in ethanol production can cause fouling of production facilities. Fouling can be caused by the precipitation of phosphate from phosphate salts (a specific type of soluble inorganic phosphorus) and calcium, magnesium, manganese or potassium onto the interior surfaces of piping, etc. Fouling can render it necessary to shut down entire ethanol production plants due to poor heat transfer and poor DDGS quality. Fouling can be especially problematic to processes where phytase is added before fermentation because large amounts of inorganic phosphate are generated from phytate degradation. Therefore, removal of soluble inorganic phosphorus could be advantageous to reduce inefficiencies and costs of fixing problems that arise in processing plants due to fouling.

A composition can be described as having a total amount of phosphorus, which is also referred to herein as total phosphorus. The total amount of phosphorous in a composition can include inorganic phosphorous and organic phosphorus. Inorganic phosphorus can be described as including both soluble inorganic phosphorus and insoluble inorganic phosphorus. Soluble inorganic phosphorus can also be referred to as reactive phosphorus. Organic phosphorus can include numerous compounds, including for example phytate. Various types of compositions can be described by the total phosphorus or other components thereof including for example distillates such as those discussed above formed from dry milling processes of corn, for example.

Disclosed herein are methods of processing distillates, methods of removing one or more forms of phosphorus from a composition, methods of obtaining phytate from distillates, methods for producing phytate derivatives, and methods of removing inorganic soluble phosphorus from distillates. Some disclosed methods can include methods of removing at least some phytate, at least some soluble inorganic phosphorus, or some combination thereof from a distillate.

Disclosed methods generally include a step of contacting a distillate or a composition containing a distillate with an anion exchange resin. A distillate as used herein can refer to something formed by distilling. Relevant distillates include some quantity of phosphorus in the form of phytate, inorganic soluble phosphate, or combinations thereof. In some embodiments, the distillate can be whole stillage (WS), thin stillage (TS), condensed distiller solubles (CDS), distillers dried grains with solubles (DDGS), or any combination thereof. In some embodiments, the distillate can be thin stillage (TS), for example.

Disclosed methods include contacting a distillate with an anion exchange resin. In some embodiments, the anion exchange resin can be a basic anion exchange resin. The anion exchange resin can be enclosed in a column, can be in a bed, or can include other types of ion exchangers. When the anion exchange resin is contacted with a composition, for example a distillate, which includes phosphorus some of the phosphorus in that composition is adsorbed onto the anion exchange resin. For example, phytate in the composition can be adsorbed onto the anion exchange resin. Because of the relatively low pH (e.g., about pH 4.4) of distillates from corn distillation (for example), most phytate that is present has already been dissolved after the fermentation of ethanol, and therefore is a negatively charged ion. Therefore, contacting the distillate with an anion exchange resin will cause at least some of the phytate (which is negatively charged) to adsorb onto the anion exchange resin. After the step of contacting the distillate with the anion exchange resin, the distillate will have less phytate present therein and the anion exchange resin will have at least some phytate adsorbed thereon. The same mechanism may explain the adsorption of soluble inorganic phosphate on the anion exchange resin.

In some embodiments, analytical grade anion exchange resins can be utilized. In some embodiments, non-analytical grade anion exchange resins can be utilized. In general, any resin designed for anion exchange can be utilized herein. In some embodiments resins in chloride form can be utilized. Specific illustrative resins that can be utilized can include those from Bio-Rad Co. (Berkeley, Calif.)—e.g., AG 1-X8; Acros Organics (Geel Belgium)—e.g., IRA-402 and IRA-900; Alfa Aesar (Ward Hill, Mass.)—e.g., IRA-68 and IRA-400; and Polysciences Inc. (Warrington, Pa.)—e.g., IRA 93, for example.

In some embodiments, particular anion exchange resins can be utilized. An example of such a particular resin is AG 1-X8 from Bio-Rad Co. This particular resin has previously been used to determine phytate in solutions. This particular resin has a strong specificity for phytate. It is also relevant that anion exchange resins have no evident adsorption effect on most nutritional ingredients, such as fat, fiber, protein, unconverted starch and metal ions. Because of the relatively low pH (4.4) in distillates from corn distillation, most phytate has already been dissolved after the fermentation of ethanol. This particular resin, AG 1-X8, was therefore utilized to extract phytate from a liquid fraction of the co-product streams.

Contact of the distillate with the anion exchange resin can be either static or dynamic. Various other conditions, including for example, time, temperature, pH, etc., can also be modified in various ways in disclosed methods. In some embodiments, the entire method can be part of a larger continuous, dynamic process or flow system. In such embodiments, some portion of the distillate can be contacted with the anion exchange resin at substantially the same time as some other portion of the distillate is separated from the anion exchange resin. Such methods can be accomplished by inserting a container or vessel (e.g., bed, column, etc.) containing an anion exchange resin into a flow through system for processing distillates (e.g., an ethanol production plant).

Contact of the distillate with an anion exchange resin can include removal of at least some of the phosphorus in the distillate. More specifically, in some embodiments contact of the distillate with an anion exchange resin can include removal of at least some of the phytate, at least some of the soluble inorganic phosphorus, or some combination thereof from the distillate. Such methods can also include removal of other forms of phosphorus from the distillate. In some embodiments, one or more forms of phosphorus are preferentially or selectively removed relative to one or more other forms of phosphorus. In some embodiments phytate is preferentially or selectively removed relative to other forms of phosphorus. In some embodiments soluble inorganic phosphorus is preferentially or selectively removed relative to other forms of phosphorus.

In some embodiments, the focus of some disclosed methods can be the distillate. For example, a disclosed method can be advantageously removing at least some portion of the phytate from a distillate. In such methods, the distillate can simply be collected once it has been contacted with the anion exchange resin. The collected distillate will have less phytate because at least some portion of the phytate originally in the distillate has been adsorbed onto the anion exchange resin. Such modified distillate can be utilized for various purposes, including for example for use as food or a food additive for animals, or for further processing to form a food or a food additive. Any processes or configurations for collecting the distillate can be utilized.

In some other embodiments, the focus of some disclosed methods can also be the distillate. For example, a disclosed method can be advantageously removing at least some portion of the soluble inorganic phosphorus from a distillate. Such methods can be utilized within a larger process, for example. As a particular example, at least some of the soluble inorganic phosphorus could be removed before the distillate is further processed in a distillate processing method, for example a process for ethanol production. The processed distillate will have less soluble inorganic phosphorus because at least some portion of the soluble inorganic phosphorus originally in the distillate has been adsorbed onto the anion exchange resin. Such modified distillates may be less likely to cause fouling of processing plants such as ethanol processing plants.

In some other embodiments, disclosed methods can be utilized to modulate the distillate to the advantage of both processing equipment and nutritional content of the modified distillate. For example, a disclosed method can be advantageously removing at least some portion of the soluble inorganic phosphorus and some portion of the phytate phosphorus from a distillate. Such methods can be utilized within a larger process, for example. As a particular example, at least some of the soluble inorganic phosphorus, the phytate phosphorus or both could be removed before the distillate is further processed in a distillate processing method, for example a process for ethanol production. The processed distillate will have less soluble inorganic phosphorus as it proceeds through the remainder of the processing equipment because at least some portion of the soluble inorganic phosphorus originally in the distillate has been adsorbed onto the anion exchange resin. Such modified distillates may be less likely to cause fouling of processing plants such as ethanol processing plants. The processed distillate will also have less phytate phosphorus but will have sufficient levels of phosphorus that the modified DDGS that will be an end product of the ethanol processing has sufficient levels of phosphorus to be useful as a nutritional source of animal feed.

Some disclosed methods can also include a step or steps of separating at least some of the distillate from the anion exchange resin. This can be accomplished by removing the anion exchange resin from the mixture of the two, by removing the distillate from the mixture of the two, or by some combination thereof. For example, if a disclosed method were part of a larger process, the anion exchange resin and the distillate could be contacted in some type of vessel or container for example (a bed containing the resin, a column containing the resin, etc.) and removal of the distillate from the anion exchange resin could be accomplished by passing the distillate therethrough by pumping, gravity, etc. Alternatively, the anion exchange resin could be removed from a vessel containing the distillate by containing the anion exchange resin in a bed that could be placed into and then removed from the vessel containing the distillate.

In some embodiments, the focus of some disclosed methods can be the phytate. For example, a disclosed method can be advantageously obtaining phytate from a distillate. The phytate can be used as obtained or can be further modified. Methods that are focused on the phytate include a step after the distillate is contacted with an anion exchange resin. Upon contacting the distillate with the anion exchange resin, the phytate will be adsorbed onto the anion exchange resin. If the phytate is the focus of the method, the phytate is then removed from the anion exchange resin. This can be accomplished by eluting the adsorbed phytate from the anion exchange resin. Generally, this can be done by contacting the adsorbed phytate on the anion exchange resin with a solution; this solution can be referred to as a desorbent or contains a desorbent. The desorbent is such that the phytate would rather be dissolved in the desorbent than be adsorbed on the anion exchange resin.

Various materials can be utilized in the desorbent. In some embodiments, an aqueous solution can be utilized. In some embodiments, an aqueous solution that contains negatively charged ions can be utilized as the desorbent. In some embodiments, an aqueous solution that contains ions having a −1 charge or −2 charge can be utilized as the desorbent. In some embodiments, an aqueous solution that contains ions having a −1 charge can be utilized as the desorbent. In some embodiments, an aqueous solution that contains fluoride ions ($F^-$), chloride ions ($Cl^-$), bromide ions ($Br^-$), iodide ions ($I^-$), hydroxide ions ($OH^-$) carbonate ions ($CO_3^{-2}$) or combinations thereof can be utilized as the desorbent. In some embodiments, an aqueous solution that contains chloride ions ($Cl^-$) can be utilized as the desorbent. In some embodiments aqueous solutions containing salts can be utilized as the desorbent. For example, aqueous solutions containing sodium chloride (NaCl), potassium chloride (KCl), hydrochloric acid (HCl), or any combination thereof can be utilized as the desorbent. For example, aqueous solutions containing sodium chloride (NaCl), potassium chloride (KCl), or any combination thereof can be utilized as the desorbent. In some embodiments, an aqueous solution that contains hydroxide ($OH^-$) can be utilized as the desorbent. In some embodiments aqueous solutions containing salts can be utilized as the desorbent. For example, aqueous solutions containing sodium hydroxide (NaOH), potassium hydroxide (KOH), or ammonia ($NH_4OH$), or any combination thereof can be utilized as the desorbent. In some embodiments, an aqueous solution that contains carbonate ($CO_3^{-2}$) can be utilized as the desorbent. In some embodiments aqueous solutions containing salts can be utilized as the desorbent. For example, aqueous solutions containing sodium carbonate ($Na_2CO_3$), potassium carbonate ($K_2CO_3$), or any combination thereof can be utilized as the desorbent.

The concentration, temperature, pH, etc., of the desorbent for eluting the phytate from the anion exchange resin (e.g., elution solution) can all be modified in various ways. The amount of desorbent necessary to remove the phytate (e.g., all of the phytate, a substantial amount of the phytate, or most of the phytate) from the anion exchange resin can also be determined.

In some embodiments, the temperature of the desorbent, the adsorbent, or the system that contains the desorbent and adsorbent can be controlled or modified. For example, in some embodiments the temperature of the desorbent, the adsorbent, or the system that contains the desorbent and adsorbent can be not greater than 70° C., not greater than 60° C., or even not greater than 50° C. In some embodiments, a distillate obtained substantially directly (in time) from processing can be cooled before or during contact with the anion exchange resin, elution of the phosphorus, or both. In such processes, distillates, for example TS, may have a temperature from 70° to 85° C.

Once the adsorbed phosphorus, for example phytate has been removed from the anion exchange resin, a phytate solution, a solution containing the phytate and the desorbent will be present. The phytate solution can be useful as such or can be further modified. In some embodiments, a phytate solution can be neutralized, for example via addition of a base, which will cause the phytate to form a salt (e.g., calcium phytate if calcium hydroxide is utilized as a base). This phytate salt can be further processed (e.g., purification methods such as recrystallization, extraction, anion exchange, etc.) to obtain phytate that can be useful on its own or further processed. In some embodiments, methods disclosed herein can produce from 1.8 to 1.9 g calcium phytate/1 kg thin stillage (TS). Phytate (regardless of purity) can be further modified, for example, by converting it into myo-inositol, which is of interest for human nutrition.

Disclosed methods can also include steps of regenerating the anion exchange resin. Often, once the adsorbed phosphorus has been removed from the anion exchange resin using the desorbent, the anion exchange resin can be contacted with a regenerating agent so that the anion exchange resin can be utilized to again remove phosphorus from a composition such as a distillate. In some embodiments the choice of regenerating agent can depend at least in part on the anion exchange resin. In some embodiments, regenerating agents can include bases or more specifically, strong bases, for example sodium hydroxide (NaOH), potassium hydroxide (KOH), or combinations thereof. In some embodiments, a solution containing the regenerating agent can be contacted with the anion exchange resin in order to render the anion exchange resin able to absorb further phosphorus from a distillate. In some embodiments, a solution of a regenerating agent at a loading rate (grams regenerating agent/liter solution) of not less than 60 g/L or not less than 80 g/L. In some embodiments, a solution of a regenerating agent at a loading rate (grams regenerating agent/liter solution) of not greater than 150 g/L, or not greater than 125 g/L can be utilized. In some embodiments the regenerating agent can be in contact with the anion exchange resin for at least 30 min. In some embodiments, the regenerating agent can have a regenerant ratio from 2 to 4% of the anion exchange resin for example.

EXAMPLES

Materials and Methods

Samples of WS, TS, WDG, CDS and DDGS were obtained from a dry milling ethanol plant located in the state of Iowa, USA. All samples were kept in the refrigerator at −20° C. for storage until analysis. Anion exchange resin AG 1-X8 (100-200 mesh, chloride form) was purchased from Bio-Rad Co. (Berkeley, Calif.) and used for phytate extraction. Phosphorus (P) kits (TNT 845/Hach, Loveland, Colo.) were used to measure the phosphorus. Sodium phytate hydrate from rice (S06880/Pfaltz&Bauer, Waterbury, Conn.) was used as standard for attenuated total reflection Fourier transform infrared spectroscopy (ATR-FTIR) analysis. All chemicals used were in analytical grade.

All samples were analyzed to quantify contents of moisture, total phosphorus and phytate phosphorus. The data for each stream was replicated three times for three independent samples.

All samples were dried in a convection oven at 105° C. until a constant weight was obtained. The moisture content was calculated by dividing the initial weight by the loss.

Total phosphorous (Total P). Total phosphorus was determined after dry-ashing samples by colorimetric assays of phosphorus in the digests. All samples were dried at 105° C. to get their dry weights. After ashing the dried mass at 550° C., $HNO_3$ was added to the remaining inorganic ash residue to convert the phosphorus residues to a dissolved phosphorus form. Total phosphorus in phosphorus acid solution was tested by phosphorus kits, of which the measurement was based on a colorimetric method where the color of the treated sample reflected the concentration of phosphorus.

Phytate phosphorous. For phytate phosphorus, aliquots of samples were extracted in 1 M HCl, phytate phosphorus was obtained as a calcium precipitate. After washing and drying the sediments, HCl was added to convert the undissolved phosphorus to a dissolved form. Total and reactive phosphorus in this phosphorus acid solution were tested by phosphorus kits. Reactive phosphorus is reported in the figures as phosphate phosphorus or simply phosphate. In these procedures, the assumption was that phosphorus in the form of phosphate and phytate would be totally precipitated. Then phytate phosphorus was calculated by subtracting the phosphate phosphorus from total phosphorus.

Solution extraction methods. Experiments were performed to compare the extraction performances by adding 1.0 mol/L (M) HCl and distilled water to extract phytate from CDS. Extracted phytate was quantified according to the procedure described above. The purpose was to prove phytate has been dissolved in the liquid fraction of the sample.

Anion exchange extraction method. For static extraction of phytate by the resin, after equilibration by 2.0 M HCl, resin AG 1-X8 was washed with distilled water until the pH was 7. Then, 10 mL liquid fraction of CDS or TS was added in 25 mL glass vials containing with 3 g (wet weight) resin. Phosphate and total phosphorus in the supernatant were tested by phosphorus kits before and after adsorption. Adsorption efficiency was evaluated by the phosphorus content change in the supernatant. Effect of time, temperature and pH on adsorption was investigated. After adsorption, the liquid fraction were removed from the vial, various desorbents (HCl, NaCl and NaOH) with different concentrations were respectively applied to elute retained phosphorus from the resin. Desorption efficiency was evaluated by the increase of phosphorus content in the desorbent. For dynamic extraction of phytate by the resin, a chromatographic column (1.0 cm×30 cm) loading with various amounts of the resin was set up. After equilibration with 2.0 M HCl, the column was washed with distilled water until the pH was 7. Then, 10 mL of the liquid fraction was sequentially passed onto the anion exchange column and then collected for phosphorus test to evaluate the adsorption efficiency at each time. The columns were washed with distilled water and the retained phytate was eluted stepwise with 10 mL 1.5 M NaCl, which was collected in 25 mL glass vials for phosphorus test to determine the desorption efficiency.

Precipitation of phytate from eluate with calcium. Precipitation of phytate was carried out by adding excess $Ca^{2+}$ into the eluate and then adjusting the pH to 7 by NaOH. After washing the sediment with distilled water, calcium phytate was obtained by drying at 105° C.

Preparation of sodium phytate from eluate. A mixed crystal of NaCl and sodium phytate was obtained by drying the eluate at 40° C., which was used as sample for ATR-FTIR analysis.

ATR-FTIR spectroscopy. The spectra were recorded in the 400 to 4000 $cm^{-1}$ range on Thermo Scientific Nicolet iS50 FTIR spectrometer (Waltham, Mass.) with a built-in diamond ATR. The background used was ambient air. The sample was tested by placing a chemical chip onto the diamond crystal window for analysis. Each test was scanned 32 times with a resolution of 0.24 $cm^{-1}$. Sodium phytate hydrate from rice was used as standard for comparison. All spectra were normalized.

Example 1

Contents of Moisture, Total Phosphorus and Phytate Phosphorus in Various Fractions of Dry Milling Process Before extraction, the first objective was to comprehend the properties of various samples. Thus, contents of moisture, total phosphorus and phytate phosphorus in various fractions were analyzed. Results are shown in Table 1 below. As the remaining part of fermentation mash after ethanol is distilled and separated, WS had 87.94% moisture content. Upon centrifugation, most solids in WS went to WDG, which resulted in that TS had 95.71% moisture content as compared to 49.75% in WDG. The moisture content of CDS and DDGS were 70.48 and 14.33%, respectively. Due to increased viscosity and osmolality, the remaining water in CDS was difficult to remove by evaporation. Usually, limited by cost in transportation for marketing, DDGS has a low moisture content which is from 10% to 15%. On the other hand, low moisture content can reduce microbial activity in DDGS, preventing it from becoming moldy and unusable.

Contents of total phosphorus and phytate phosphorus were performed on a dry basis (db). As shown in Table 1, WS had 12.02±0.60 mg P/g db total phosphorus and 4.81±0.01 mg P/g db phytate phosphorus, whereas TS had 23.57±1.12 and 10.11±0.66 mg P/g db, respectively. The increase was mainly due to more phosphorus going to the liquid fraction (TS) than the solid fraction (WDG) during the centrifugation of WS. Evaporation caused little change in phosphorus profile, so CDS had similar contents with TS in both total phosphorus and phytate phosphorus. Upon mixing CDS with WDG and drying the mixture into DDGS, the contents of both total phosphorus and phytate phosphorus reached the initial value but a little less than those of WS, this difference may have been due to recycling a portion of TS as a backset for cooking step.

TABLE 1

Moisture, total phosphorus and phytate phosphorus in various fractions of dry milling process

| Stream name | Moisture content (wt. %) | Total phosphorus (mg P/g sample) | Phytate phosphorus (mg P/g sample) |
| --- | --- | --- | --- |
| WS | 87.94 ± 0.15 | 12.02 ± 0.60 | 4.81 ± 0.01 |
| TS | 95.71 ± 0.13 | 23.57 ± 1.12 | 10.11 ± 0.66 |
| WDG | 49.75 ± 0.40 | 10.21 ± 0.53 | 3.27 ± 0.21 |
| CDS | 70.48 ± 0.22 | 23.77 ± 0.23 | 9.41 ± 0.34 |
| DDGS | 14.33 ± 0.39 | 10.59 ± 0.20 | 4.50 ± 0.15 |

Example 2

Extraction of Phytate Via the Addition of Acid and Water

With the addition of 60 mL of 1 M HCl and distilled water into 30 g CDS, phytate was extracted at 150 rpm, 30° C. for 2 h. As shown in FIG. 1, the phytate concentrations in two extracts had a relatively insignificant difference, which indicated that most phytate had already been dissolved in the liquid fraction. This dissolution was most likely attributed to the low pH (4.4) of CDS. Such would explain why the strong acid lead to no evident increase in the phytate concentration of the extract. Since centrifugation and evaporation caused little change in pH, the pH of TS and WS were 4.47 and 4.48, respectively, most phytate likely exists in an anionic form in TS and WS. Thereby, it is reasonable to understand that the difference between TS and WDG in phytate content is generally a result of most phytate going to the TS with the liquid fraction. It has been previously reported that 82% of total phosphorus in WS was in the water part, which also understandably supports this viewpoint.

Example 3

Static Extraction of Phytate by Anion Exchange Resin

Figure 2A:
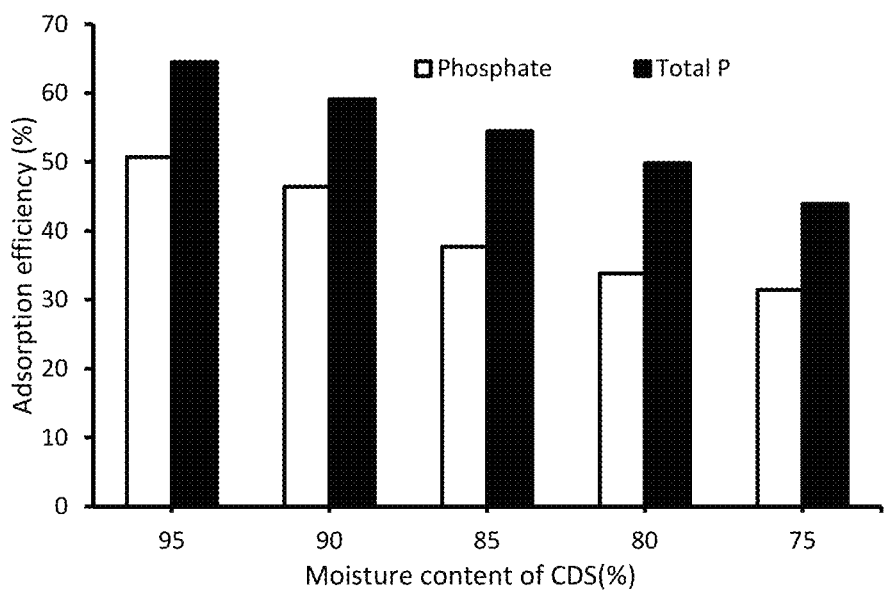
FIGS. 2A, 2B, 2C and 2C show the effect of phosphorus (P) concentration, temperature, time and pH on adsorption efficiency of phosphate and total phosphorus (correlation between adsorption efficiency and liquid fraction from CDS with various moisture content (FIG. 2A); correlation between adsorption efficiency and adsorption temperature (FIG. 2B); correlation between adsorption efficiency and adsorption time (FIG. 2C); and correlation between adsorption efficiency and adsorption pH (FIG. 2D)).

In order to study the effect of the phosphorus (P) concentration on adsorption, phosphorus solutions with various concentrations were obtained by diluting CDS with distilled water and then separating the liquid fraction via centrifugation and filtration (0.45 μm). The moisture content of diluted CDS indirectly reflected the concentration of phosphorus. As shown in FIG. 2A, resin AG 1-X8 showed a better adsorption performance with phosphorus solutions at lower concentrations. The highest adsorption efficiency of phosphate and total phosphorus was attained on diluted CDS with 95% moisture content which was very close to that of TS (95.71%). Since CDS was generated by evaporation of TS, similar adsorption performances would be logically achieved on liquid fraction of TS and diluted CDS with 95% moisture content. As demonstrated in Table 1 above, TS was the stream with the highest moisture content in the forming process of DDGS. In the dry milling process, approximately 75% of the phosphorus flows into TS after centrifugation of WS as compared to about 25% into the WDG. If most phytate in the TS could be extracted, the final content of phytate in DDGS would be drastically decreased. Therefore, the liquid fraction of TS was used as feedstock in subsequent extraction experiments.

Figure 2B:
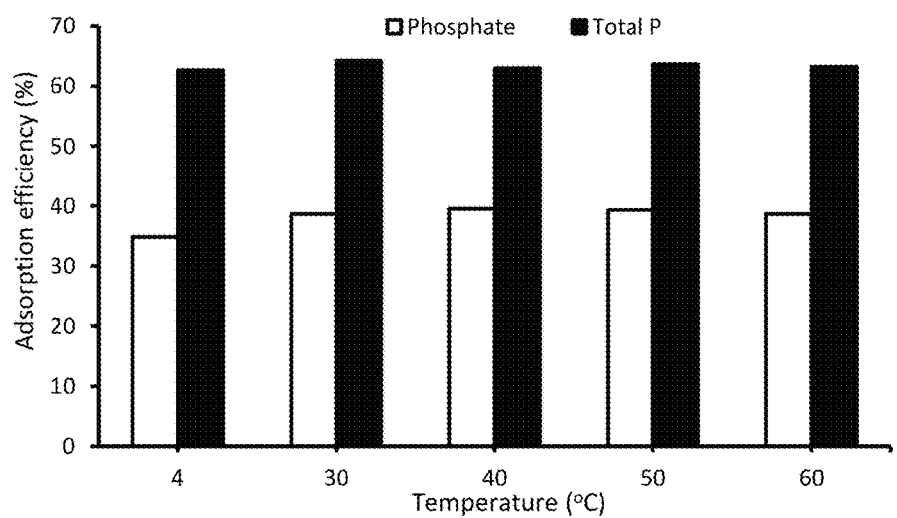
Figure 2C:
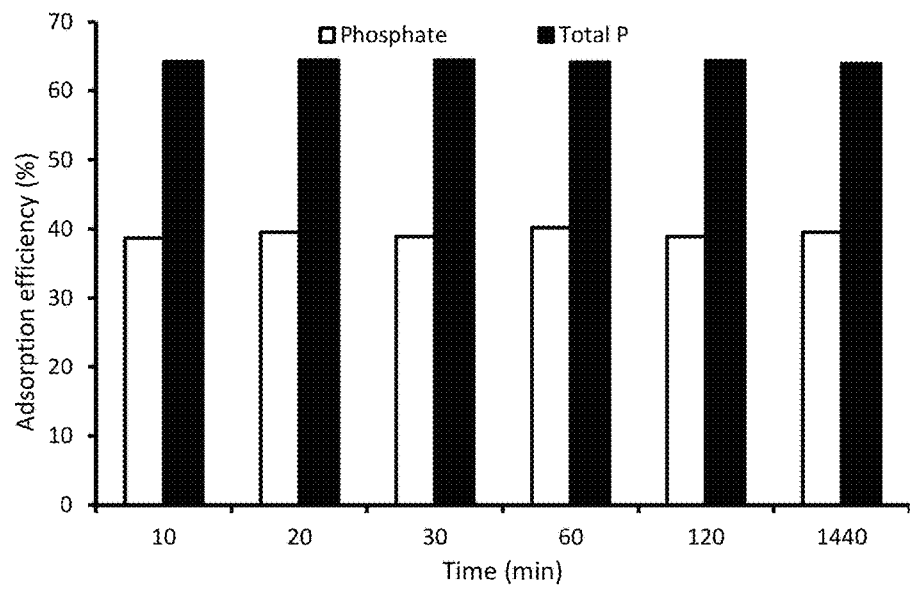
Figure 2D:
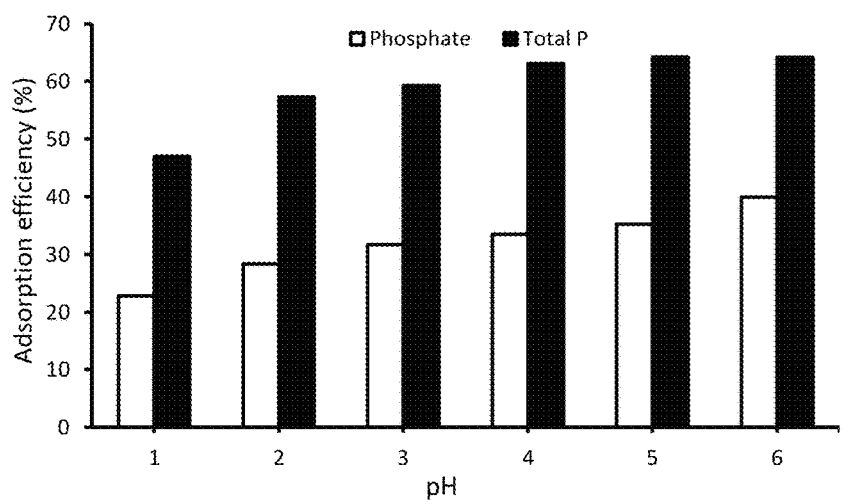

FIG. 2B shows that the extraction can be accomplished at room temperature (25° C.). Due to the high specific surface area of the resin, static adsorption was mostly complete in 10 min (FIG. 2C). To study the effect of pH in adsorption, phosphorus solutions having a pH ranging from 1 to 6 were prepared by adding appropriate amounts of NaOH or HCl to liquid fractions of TS. The liquid fractions at different pH levels were then applied to vials containing AG 1-X8 resin. As shown in FIG. 2D, more phosphorus (mainly in phosphate and phytate anion form) was adsorbed to the resin when the liquid fraction of TS was applied at higher pH than at lower pH, as would be expected. For phosphorus in phosphate and phytate form, the adsorption that occurs on the AG 1-X8 resin mainly depends on the electronegativity of each anion undergoing exchange with chloride ions ($Cl^-$). Since a higher pH favors ionization of both phosphate and phytate by dissociating $H^+$ from the hydroxyls, an increase in the ability of anions to go through the exchange with an augment of electronegativity is obtained. For the liquid fraction of TS, sediment would appear when pH was over 7, which should create a hurdle for the adsorption. The resin presented a good adsorption performance when the pH was from 4 to 6 (FIG. 2D). Since the pH of TS was 4.47, no pH adjustment was needed before adsorption.

Figure 3A:
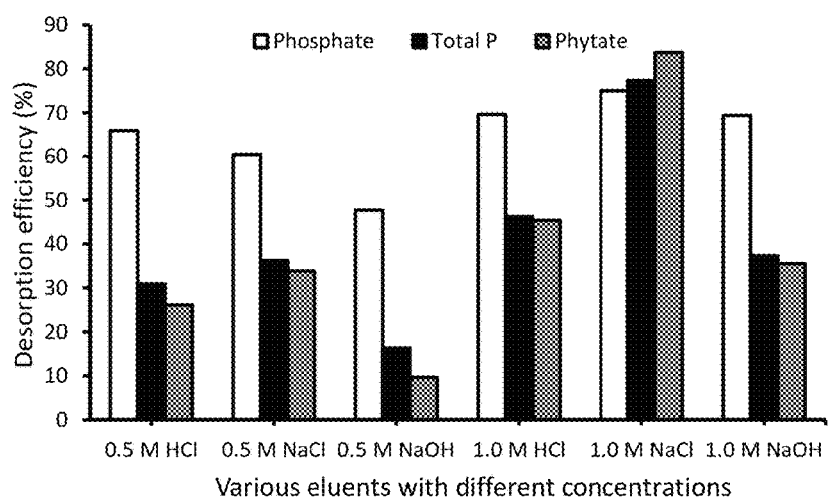
FIGS. 3A and 3B show the effect of various desorbents with different concentrations on desorption efficiency of phosphate, total phosphorus and phytate (correlation between desorption efficiency and various desorbents with different concentrations (FIG. 3a); and correlation between desorption efficiency and concentration of NaCl (FIG. 3b)).
Figure 3B:
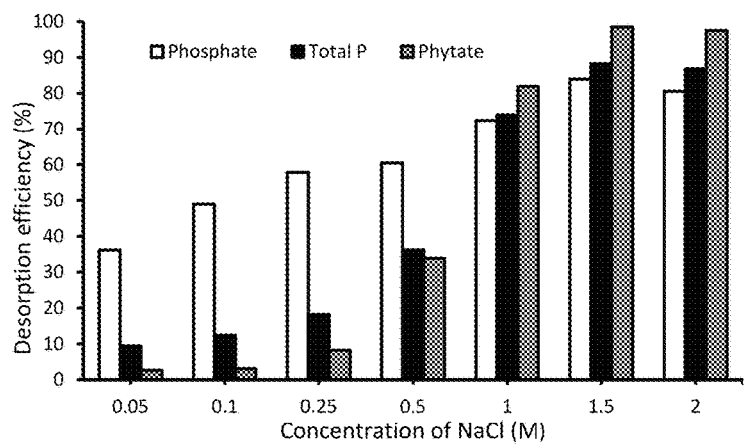

For the desorption of phosphorus from the resin, desorption efficiency of phytate was calculated on the basis of an assumption that only phosphorus in phosphate and phytate forms could be adsorbed by the resin. Adsorbed phytate was calculated by subtracting the adsorbed phosphate phosphorus from adsorbed total phosphorus. NaCl exhibited a better desorption performance on adsorbed phytate with both 0.5 and 1.0 M concentration as compared to HCl and NaOH (FIG. 3A). FIG. 3B demonstrated that the highest desorption efficiency of phytate was attained when the concentration of NaCl was over 1.5 M. Thereby, 1.5 M NaCl was used as desorbent in subsequent dynamic phytate extraction experiments.

Example 4

Dynamic Extraction of Phytate by Anion Exchange Resin

Figure 4:
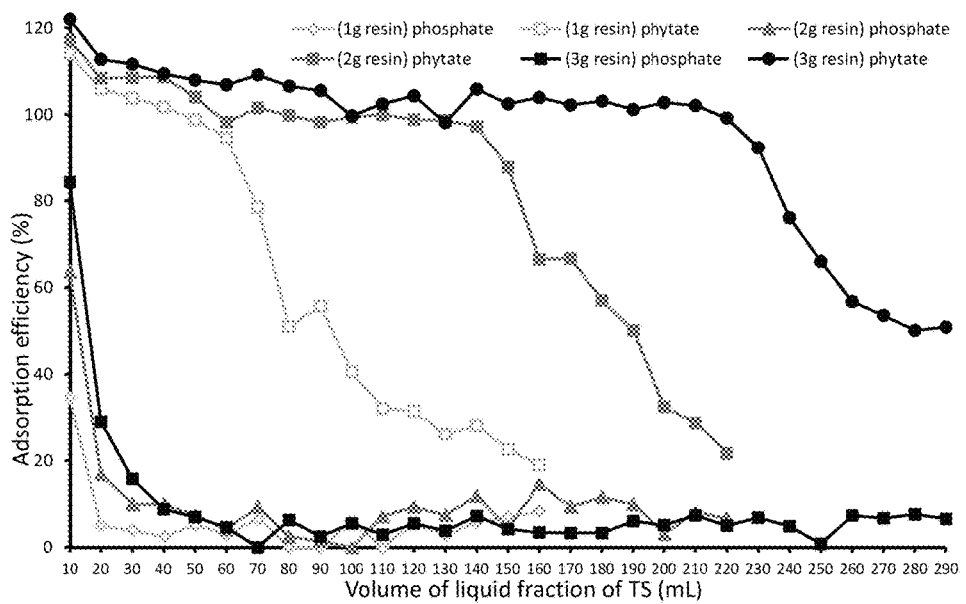
FIG. 4 shows the effect of the amount of resin packed in the column on adsorption efficiency of phosphate and phytate.

Chromatographic columns containing various amounts of AG 1-X8 resin was used for dynamic extractions from liquid fractions of TS. From the dynamic adsorption curves presented on FIG. 4, it was observed that the resin had a more powerful absorbability on phytate than phosphate. This was mainly attributed to the more charged oxygen on the phytate molecule than on the phosphate molecule. As shown in FIG. 4, the adsorption efficiency of phytate was sometimes over 100%. The excessive contribution was probably from phosphorus in other forms that could also be adsorbed on the resin, which was considered as phytate based on the assumption mentioned above. The inflexion of the adsorption curve starting to decrease gradually was defined as the penetrating capacity. For the column containing 1 g resin, the penetrating capacity for phytate was about 50 mL/g (TS/resin). It increased to 70 and 73 mL/g for columns containing 2 and 3 g resin. The increase might arise from additional adsorption time caused by more resin packed in the column.

Figure 5:
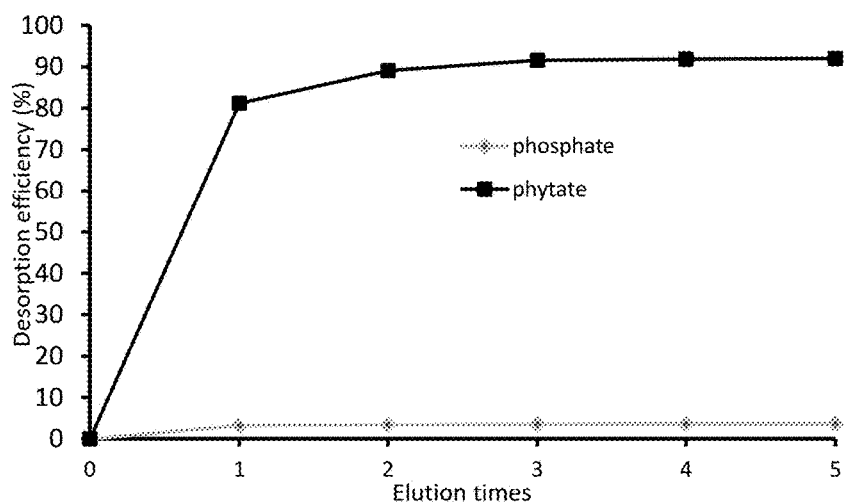
FIG. 5 shows the effect of elution time on desorption efficiency of phosphate and phytate.

For the column containing 3 g resin, approximately 100% of phytate and 6.15% of phosphate were adsorbed after 220 mL liquid fraction of TS was passed stepwise onto the column (FIG. 5). Over 91% of the retained phytate was eluted from the resin with stepwise addition of 3 times 10 mL of 1.5 M NaCl. Whereas, only about 3.5% of the retained phytate was simultaneously eluted, which meant most phosphorus in the eluate was in phytate form and calcium phytate with high purity would be theoretically obtained after undergoing the precipitation step described above.

Example 5

ATR-FTIR Analysis of Extracted Phytate

Figure 6:
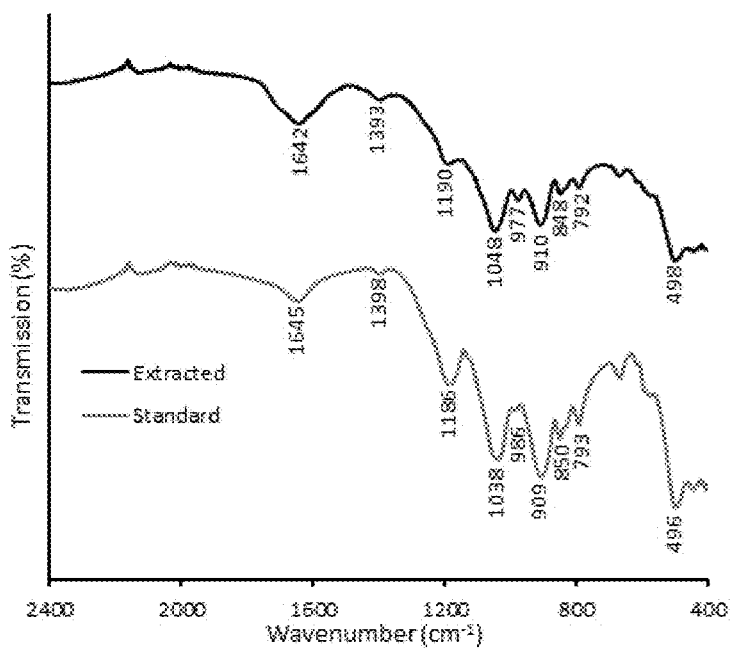
FIG. 6 shows a comparison of Fourier transform infrared (FTIR) spectra of sodium phytate prepared from the eluate and standard sodium phytate.

The ATR-FTIR spectra of standard sodium phytate and extracted sodium phytate are shown in FIG. 6. A weak absorption band around 1645 cm$^{-1}$ and a broad absorption band at 3400 cm$^{-1}$ (data not shown) are present due to the existence of O—H bonds which might be from the adsorbed water molecules. The absorption band around 1398 cm$^{-1}$ was assigned to the C—O stretching vibration. Two bands around 1186 and 496 cm$^{-1}$ were most likely attributed to $PO_4^{2-}$ groups. The bands around 1038, 986, 909, 850 and 793 cm$^{-1}$ were assigned to the C—O—P vibrations from various types of phytate (IP2-IP6). The small shifts in the vibrational bands between two kinds of sodium phytate were possibly due to the sodium chloride mixed in the extracted one and different structures of phytate in samples. Thus, extracted phytate was confirmed as the ATR-FTIR spectrum was consistent with that of the standard.

Example 6

Purification of Phytate from the Eluate

Precipitation of phytate with $Ca^{2+}$ from the eluate would not only remove the Cl$^-$ brought with the desorption method, but also implement the discoloration via removal of some organic molecules which could be adsorbed to, and eluted from the resin. 0.49 g calcium phytate was obtained from the 30 mL eluate mentioned above. As 220 mL liquid fraction of TS, where the eluate was from, was prepared with 265 g TS by centrifugation and filtration, 1.85 g calcium phytate could be theoretically prepared from 1 kg TS (wet weight) with this method. Based on the assumption that $Ca_6IP6$ was the only form of phytate existing in the final product, 0.39 g phytate phosphorus was removed from 1 kg (wet weight) TS.

The above results shows that almost all of the phytate phosphorus in the liquid fraction of TS was removed using disclosed methods. Additionally, calcium phytate was acquired as a value-added product.

Example 7

Effect of Resin Type on Phytate Adsorption

Sample of thin stillage (TS) was obtained from a dry milling ethanol plant located in the state of Minnesota, USA. The TS was kept in the refrigerator at −20° C. for storage until analysis. Anion exchange resins IRA-402 and IRA-900 were purchased from Acroc Organics (Geel, Belgium), IRA-68 and IRA-400 were purchased from Alfa Aesar (Ward Hill, Mass.) and IRA-93 was purchased from Polysciences Inc. (Warrington, Pa.). All the resins were in chloride form. Phosphorous (P) kits (TNT 845/Hach, Loveland, Colo.) were used to measure the phosphorus. All chemicals used were analytical grade and were used as is.

Static Extraction of Phytate. The resins were equilibrated using 2.0 M HCl and then washed with distilled water until the pH of the rinse solution was about 7. Then, 10 mL liquid fractions of CDS or TS were added to 25 mL glass vials that contained 3 g (wet weight) resin. Phosphate and total phosphorus in the supernatant were tested by phosphorus kits before and after adsorption. Adsorption efficiency was evaluated by the phosphorus content change in the supernatant. Effect of time, temperature and pH on adsorption was also investigated. After adsorption, the liquid fraction was removed from the vial, and various desorbents (HCl, NaCl and NaOH) were applied to elute retained phosphorus from the resin. Desorption efficiency was evaluated by the increase of phosphorus content in the eluent (the eluent includes the desorbent and any components removed from the anion exchange resin by the desorbent). Both adsorption and desorption efficiency of phytate was calculated on the basis of the assumption that only phosphorus in phosphate and phytate form could be adsorbed by the resin. Adsorbed phytate was calculated by subtracting the adsorbed phosphate phosphorus from adsorbed total phosphorus. Desorbed phytate was calculated by subtracting the desorbed phosphate phosphorus from desorbed total phosphorus.

Dynamic Extraction of Phytate. The resins were loaded in a chromatographic column (1.0 cm×30 cm) at various levels. After equilibration with 2.0 M HCl, the column was washed with distilled water until the pH of the rinse solution was about 7. Then, 10 mL of the liquid fraction was sequentially passed onto the anion exchange column and then collected for phosphorus test to evaluate the adsorption efficiency at desired time intervals. The column was washed with distilled water and the retained phytate was eluted stepwise with 10 mL 2.5 M HCl, which was collected in 25 mL glass vials for phosphorus test to determine the desorption efficiency.

Precipitation of phytate from eluate with calcium. The phytate was precipitated by adding excess $Ca^{2+}$ into the eluate and then adjusting the pH to about 7 with NaOH. After washing the sediment with distilled water, calcium phytate was obtained by drying at 105° C.

Figure 7:
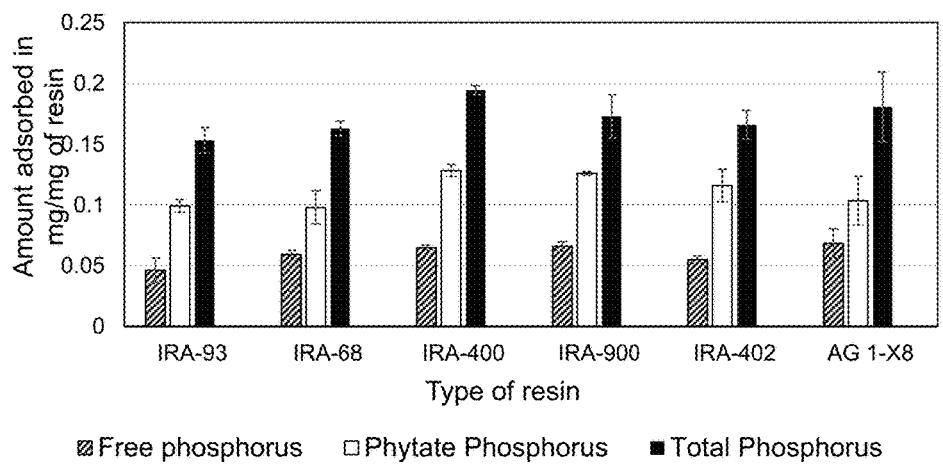
FIG. 7 shows the amount of various types of phosphorus adsorbed (mg) per mg resin for different resins.

The following resins: IRA-93, IRA-68, IRA-900, IRA-400, IRA-402, AG 1-X8, which are all alkali type resins were selected to investigate their adsorption capacity. Phytate and reactive phosphorus were extracted from TS distillates onto the resins as described above. For some considerations, resins capable of adsorbing relatively more phytate and less reactive phosphorus may be more advantageous. The adsorption capacity of the resins are shown in FIG. 7. The IRA-400 (0.128 mg phytate/mg resin) and IRA-900 (0.126 mg phytate/mg resin) resins adsorbed the most phytate per mass of resin, but IRA-900 (0.733 phytate phosphorous/total phosphorous) showed more selectivity compared to the IRA-400 (0.661 phytate phosphorous/total phosphorous) resin is this experiment (FIG. 8).

Figure 8:
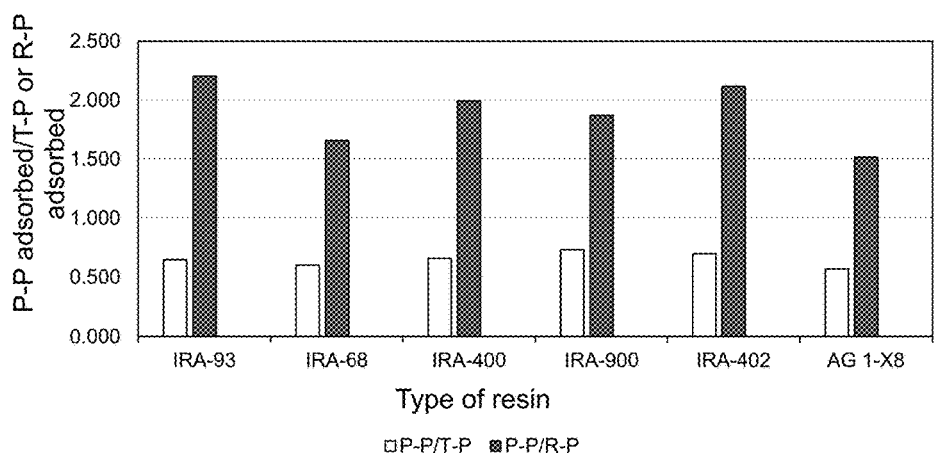
FIG. 8 shows the amount of phytate phosphorus (P-P) relative to total phosphorus (T-P) and phytate phosphorus relative to reactive phosphorus (R-P) adsorbed by different types of resins.

This example also shows that reactive phosphorus or soluble inorganic phosphorus can be adsorbed onto anion exchange resins (as seen in FIG. 8). For example, approximately 37% of the total phosphorus adsorbed at equilibrium conditions on AG 1-X8 resin at scarced resin conditions (i.e., in conditions in which the amount of resin present in the experiment is below the amount necessary to promote a full removal of phytate), 37% of total phosphorus adsorbed is reactive phosphorus.

In total, 80.3% total phosphorus (T-P) can be removed upon saturation of the resin (3 g of resin to treat 175 mL of TS). Removal of this amount of total phosphorus can significantly decrease the phosphate precipitation and concomitant fouling effects while still maintaining a sufficient amount of phosphorus in the DDGS end products for nutritional use as animal feed.

Example 9

Effect of Various Conditions on Adsorption/Desorption

Figure 9:
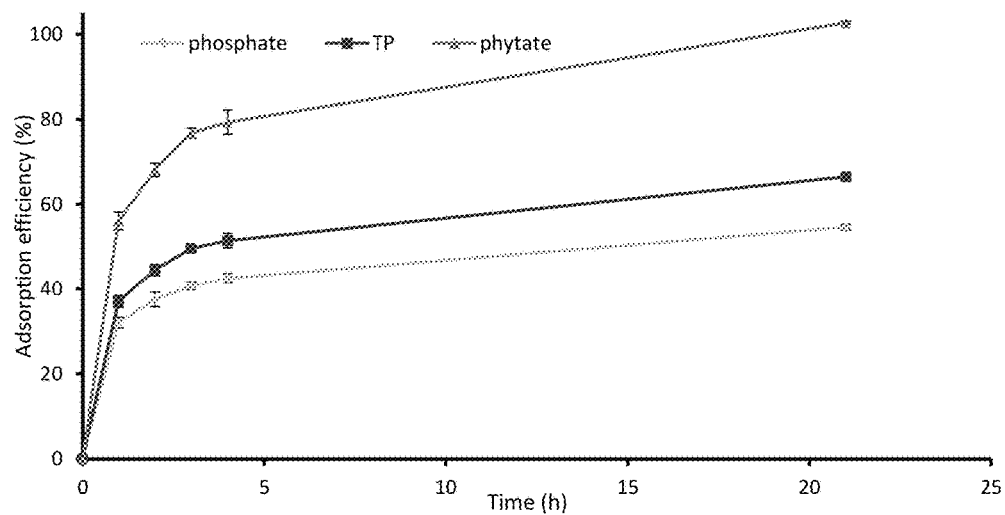
FIG. 9 shows the correlation between adsorption efficiency and time; adsorption conditions were 10 mL liquid fraction of TS mixed with 3 g resin (wet weight) at room temperature for different time.

Effect of time on phytate adsorption. The adsorption kinetic of resin IRA-93 on phytate and phosphate is shown in FIG. 9. Both phytate and phosphate were adsorbed rapidly by resin IRA-93. Within 2 h, the adsorption levels had increased sharply. The adsorption rate gradually slowed down and adsorption efficiency finally reached 100% at 21 h, which suggested that the adsorption equilibrium occurred between 5 and 21 h. As shown in FIG. 9, at 21 h, phytate was completely adsorbed on the resin, as compared to 54.7% of phosphate was adsorbed. The difference was mainly attributed to the more charged oxygen on the phytate molecule than on the phosphate molecule, which resulted in a stronger competitiveness of phytate on anion exchange.

Figure 10:
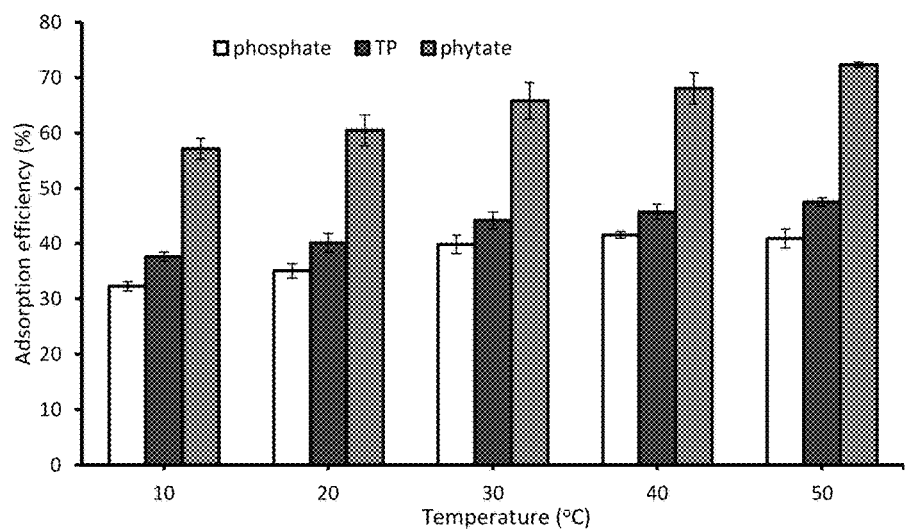
FIG. 10 shows the correlation between adsorption efficiency and temperature; adsorption conditions were 10 mL liquid fraction of TS mixed with 3 g resin (wet weight) at different temperature for 1 h.

Effect of temperature on phytate adsorption. Temperature may be a factor that could influence the adsorption capacity. As shown in FIG. 10, the adsorption capacity rose as the temperature increased. This was presumably due to the increasing kinetic energies of phytate molecules caused by higher temperature, which accelerated the relative speed of movement of the molecules. The result also indicated that the adsorption process was an endothermic reaction, namely, a relatively high temperature facilitated the phytate adsorption with resin IRA-93. Since commercial TS temperature varies from 70 to 85° C., in dry milling process, potentially, an anion exchange step can be carried out for phytate extraction with cooling TS down.

Figure 11:
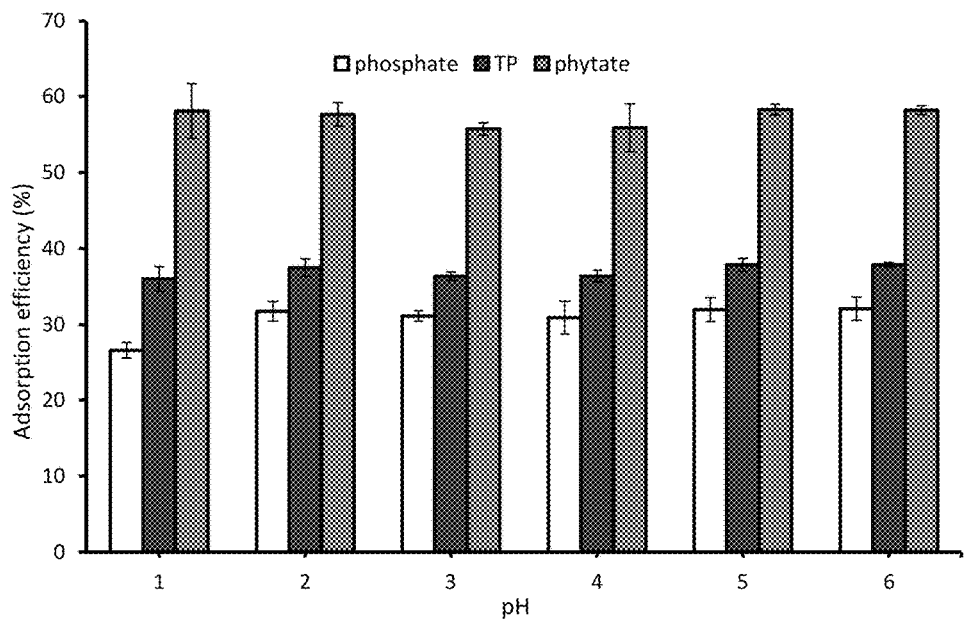
FIG. 11 shows the correlation between adsorption efficiency and pH of TS; adsorption conditions were 10 mL liquid fraction of TS at different pH level mixed with 3 g resin (wet weight) at room temperature for 1 h.

Effect of TS pH on phytate adsorption. Liquid fractions of TS with pH ranging from 1 to 6 were prepared by adding appropriate amounts of NaOH or HCl to liquid fraction of TS. Then the liquid fraction at different pH levels was applied to vials containing with resin IRA-93. As shown in FIG. 11, pH did not show any significant influence on the adsorption capacity, which suggested resin IRA-93 had a remarkable applicability of pH on phytate adsorption. Since the pH of TS was 4.47, no pH adjustment was needed before adsorption.

Figure 12:
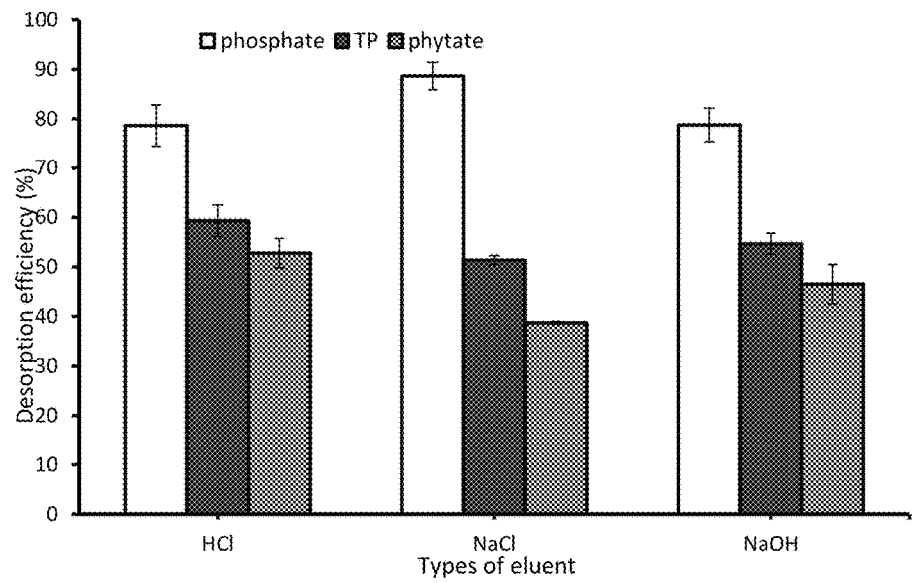
FIG. 12 shows the correlation between desorption efficiency and various desorbents; desorption conditions were 3 g resin (wet weight) adsorbed with phosphorus mixed with 1 M of different desorbents at room temperature for 1 h.

Effect of desorbent type on phytate desorption. 1.0 M HCl, NaCl and NaOH were respectively applied to elute retained phosphorus from the resin. HCl exhibited a better desorption performance on adsorbed phytate as compared to HCl and NaOH (FIG. 12). Therefore, HCl was used as desorbent for phytate desorption in subsequent experiment.

Figure 13:
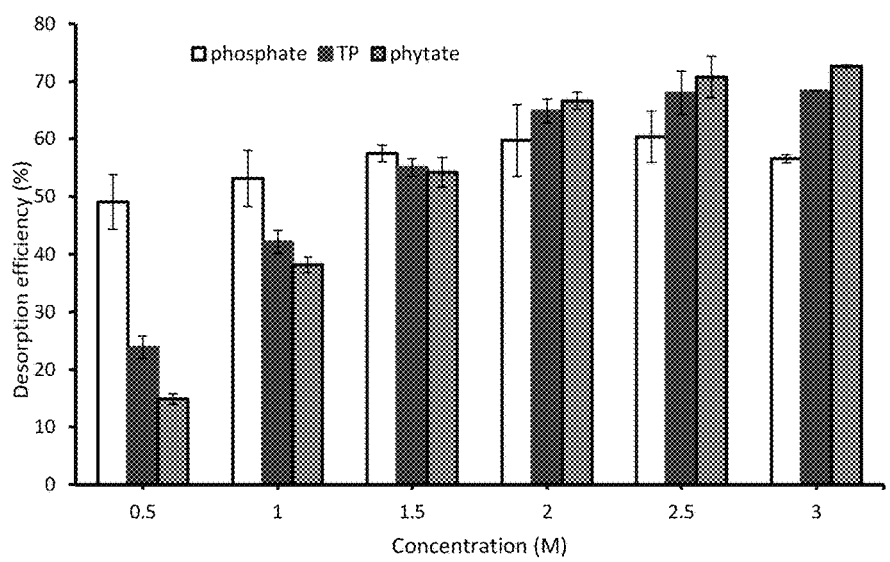
FIG. 13 shows the correlation between desorption efficiency and concentration of HCl; desorption conditions were 3 g resin (wet weight) adsorbed with phosphorus mixed with different concentrations of HCl at room temperature for 1 h.
Figure 14A:
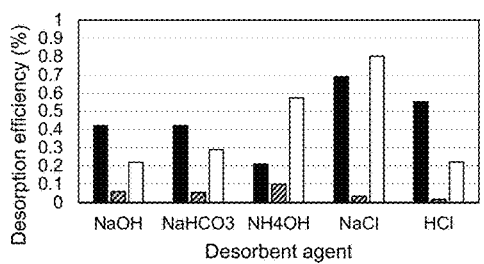
FIGS. 14A to 14E show desorption efficiency (%) for IRA 93 (FIG. 14A), IRA 68 (FIG. 14B), IRA 900 (FIG. 14C), IRA 400 (FIG. 14D) and IRA 402 (FIG. 14E) using different desorption agents.
Figure 14B:
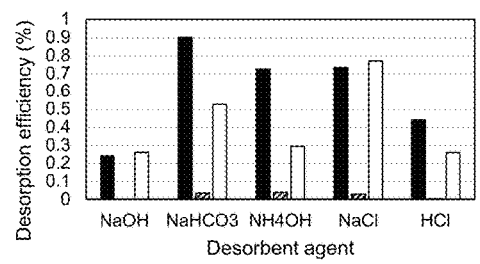
Figure 14C:
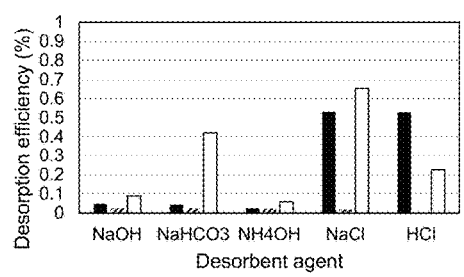
Figure 14D:
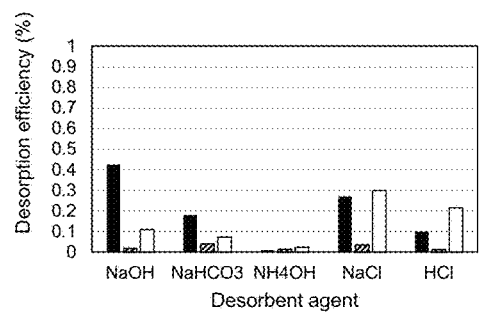
Figure 14E:
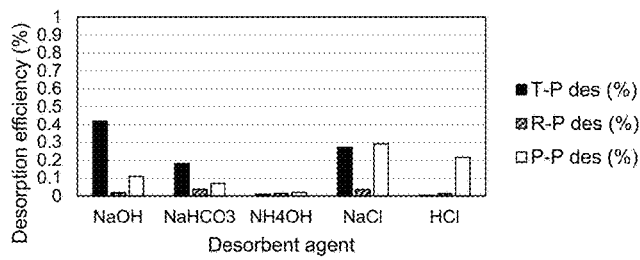

Effect of HCl concentration on phytate desorption. As shown in FIG. 13, the desorption efficiency dramatically increased as the HCl concentration rose from 0.5 to 2.5 M. The desorption efficiency did not significantly change when the HCl concentration continued to increase to 3.0 M. Thereby, 2.5 M HCl was used as desorbent in subsequent dynamic phytate extraction experiments.

Example 10

Desorption

Figure 15:
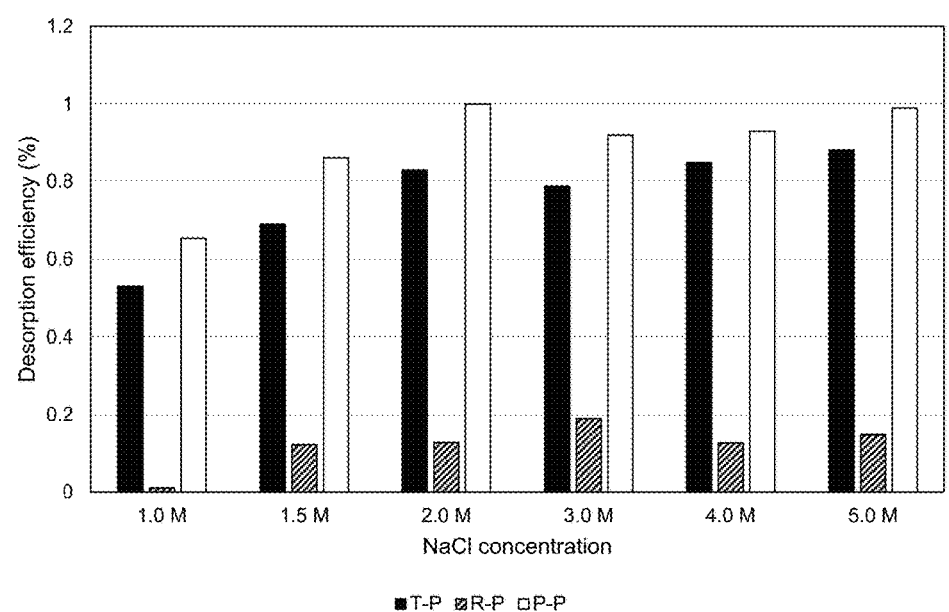
FIG. 15 shows desorption efficiency (%) of total phosphorus (T-P), reactive phosphorus (R-P) and phytate phosphorus (P-P) at different NaCl (desorption agent) concentrations.
Figure 16A:
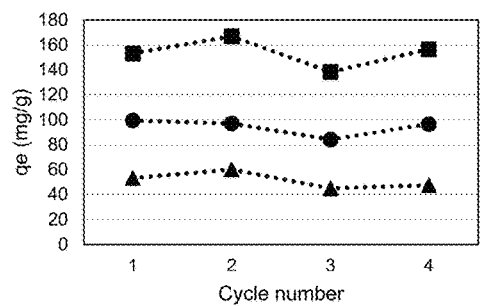
FIGS. 16A to 16E shows equilibrium concentrations (qe) of phytate-phosphorus (P-P), reactive phosphorus (R-P) and total phosphorus (P-P) in (mg/g resin) for four cycles on for IRA 93 (FIG. 16A), IRA 68 (FIG. 16B), IRA 900 (FIG. 16C), IRA 400 (FIG. 16D) and IRA 402 (FIG. 16E).
Figure 16B:
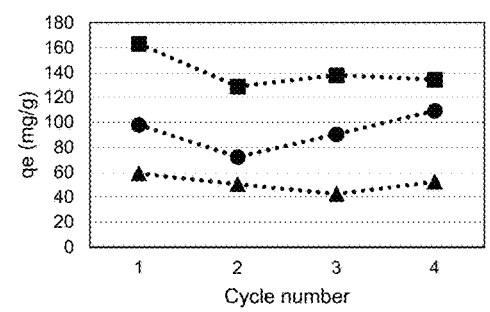
Figure 16C:
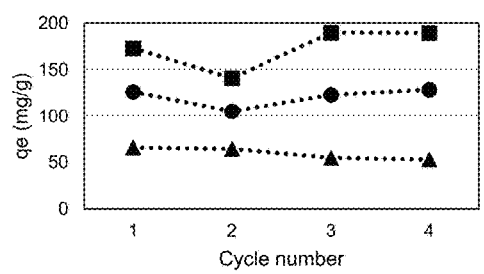
Figure 16D:
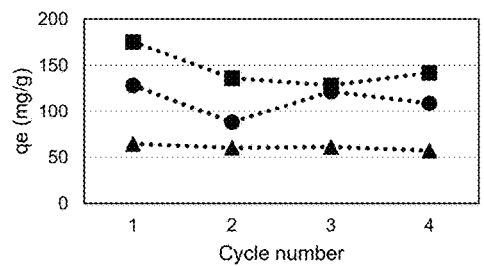
Figure 16E:
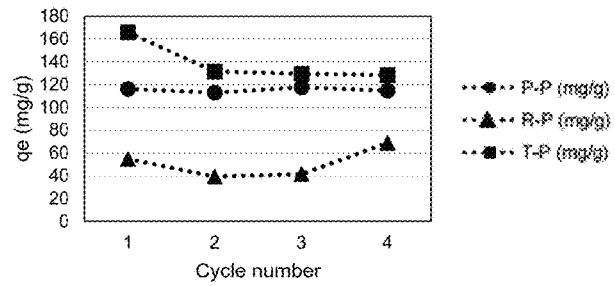

Possible desorbents can be based, at least in part, on cost-effectiveness and efficiency of desorbing phytate from the resin into the eluent for final product recovery. Different types of desorbents (NaOH, NaCl, $Na_2CO_3$, HCl, and $NH_4OH$), at 1.0 mol $L^{-1}$ concentrations were tested to evaluate the desorption capacity in all the six resins. The phytate-phosphorus desorption was found to be more effective and selective with NaCl in all resins tested (FIGS. 14A to 14E), and as a result, was selected as the desorbing agent for further studies. The desorption efficiency is a function of the concentration of desorbent agent and the amount of phytate-phosphorus adsorbed by the resin. Since IRA-900 shows better phytate-phosphorus adsorption and selectivity, the concentration of the NaCl was varied from 1 to 5 M (FIG. 15) to achieve better desorption. With 2M NaCl, 100% desorption of Phytate-phosphorus was achieved with the IRA-900 resin.

Example 11

Regeneration of Anion Exchange Resins

It may be advantageous for a resin to have an extended lifespan in order to reduce the operating cost of the adsorption process and to achieve technical feasibility. A study was therefore conducted to evaluate the regeneration capacity of the 5 macroporous (IRA series) resins using NaCl (2 mol $L^{-1}$) as desorbent and NaOH (150 g $L^{-1}$ at a loading rate of 4%) as a regenerating agent for 4 cycles of operation. The equilibrium concentrations (qe) of phytate-phosphorus (mg/g resin) in all the four cycles for all the resins tested, were within 2.5 standard deviations from the mean, which is an acceptable deviation for this study (FIG. 16A to 16E). The adsorption-desorption capacity and selectivity were similar for all 4 cycles.

Example 12

Dynamic Extraction of Phytate with Anion Exchange Resin

Figure 17:
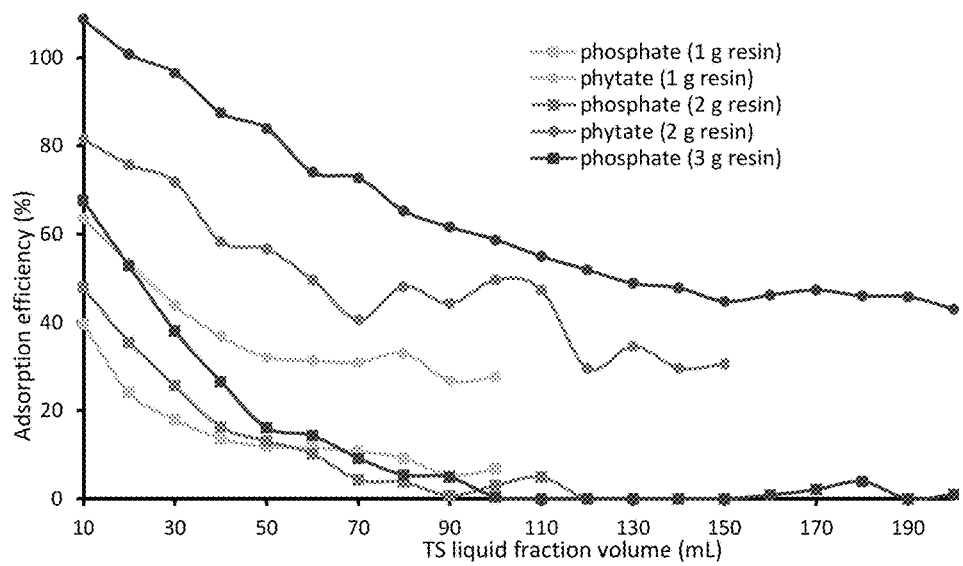
FIG. 17 shows the effect of the amount of resin packed in the column on the adsorption efficiency of phosphate and phytate.

Effect of flow speed on phytate desorption. Chromatographic columns respectively containing various amounts of resin IRA-93 were carried out for dynamic extraction from liquid fraction of TS. From the dynamic adsorption curves presented on FIG. 17, it could be seen that the resin had a more powerful absorbability on phytate than phosphate. As was mentioned before, this was mainly attributed to the more charged oxygen on the phytate molecule than on the phosphate molecule. As shown in FIG. 17, the adsorption efficiency of phytate was sometimes over 100%, the excessive contribution was probably from phosphorus in other forms that could also be adsorbed on the resin, which was considered as phytate based on the assumption mentioned above. The adsorption efficiency rose as the amount of resin increased, the increase was most likely due to the slower flow speed caused by more resin packed in the column.

Figure 18:
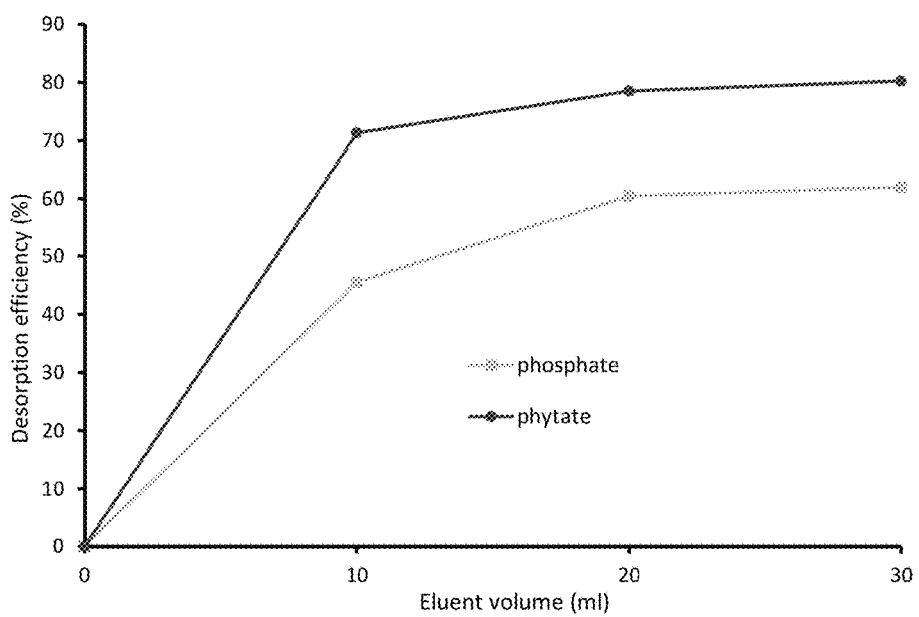
FIG. 18 shows the effect of elution time on desorption efficiency of phosphate and phytate.

Dynamic adsorption and desorption properties under optimum conditions. For the column containing with 3 g resin, 94.37% of phytate and 50.35% of phosphate were adsorbed on after 30 mL liquid fraction of TS stepwise passing onto (FIG. 18). About 80% of retained phytate was eluted from the resin with stepwise adding 10 mL 2.5 M HCl for three times. Whereas, about 60% of retained phytate was simultaneously eluted.

After going through the precipitation step described above, 0.0878 g sediment was obtained from the 30 mL eluate mentioned in Section 3.4. As 30 mL liquid fraction of TS, where the eluate was from, was prepared with 36 g TS, 2.44 g sediment could be theoretically prepared from 1 kg TS (wet weight) with this method.

Example 13

Breakthrough Profile on IRA-900 Packed Column

Figure 19:
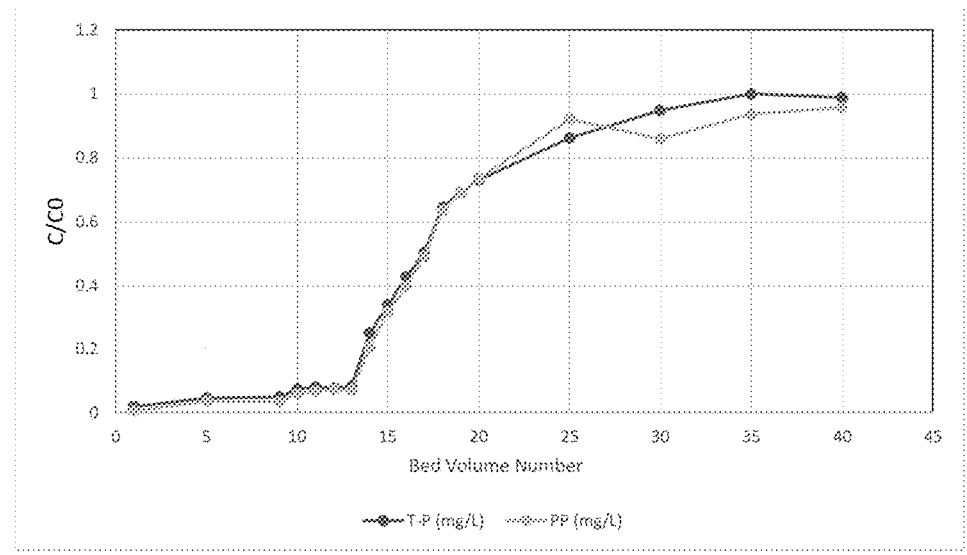
FIG. 19 shows the concentration of phytate in the effluent (C) relative to the initial concentration (C0) for total phosphorus (T-P) and phytate phosphorus (PP) as a function of bed volume number.

When the thin stillage liquid is fed to a IRA-900 packed column, it will exchange all its exchangeable ions in a narrow zone at the top of the packed bed. This solution is then passed through the lower part of the column without further change in composition. As the feed is continued, the top layers of the bed are exposed to fresh solution. Eventually, all the phytate and the total phosphorus are adsorbed and the resin loses its efficiency. The zone in which the ion exchange occurs is thus displaced downstream on the column. In due course, this zone reaches the bottom of the column. The profile relating the concentration of phytate and total phosphorus over the volume eluted is called breakthrough. The results can be seen in FIG. 19. In FIG. 19, the y-axis relates the ratio of concentration in the effluent, C, with the initial concentration, C0, for Total Phosphorus (TP) and Phytate Phosphorus (PP).

Example 14

Elution Profile on IRA-900 Resin

Figure 20:
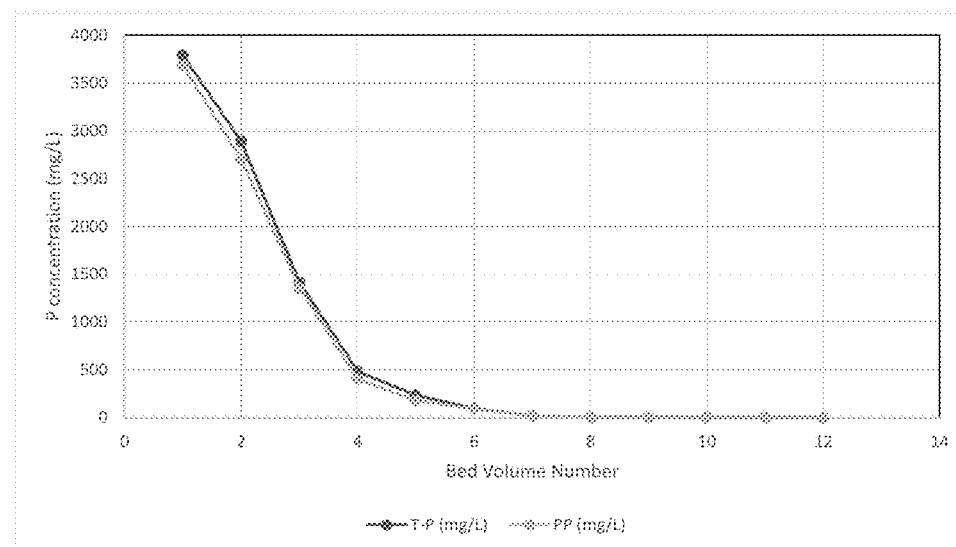
FIG. 20 shows the desorption of adsorbed total phosphorus (T-P) and phytate phosphorus (P-P) on an IRA-900 resin using NaCl (2 mol $L^{-1}$) on a packed column.

Dynamic elution. Desorption of adsorbed phytate on IRA-900 resin was evaluated using NaCl (2 mol $L^{-1}$) on a packed column. The initial high concentrations of phytate and total phosphorus are sequentially decreased to lower concentrations. The results are seen in FIG. 20.

Figure 21:
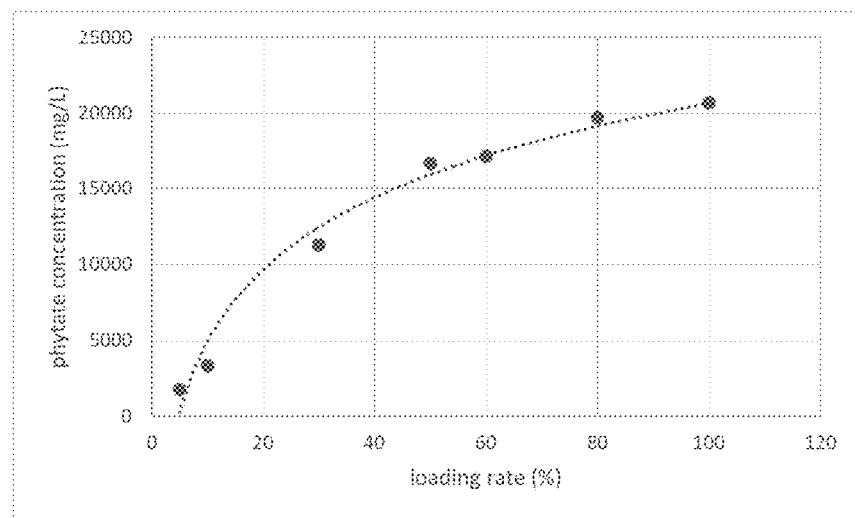
FIG. 21 shows the phytate concentration (mg/L) as a function of resin loading rate (%), which was considered the amount of resin in grams present in 100 mL of desorbent.
Figure 22:
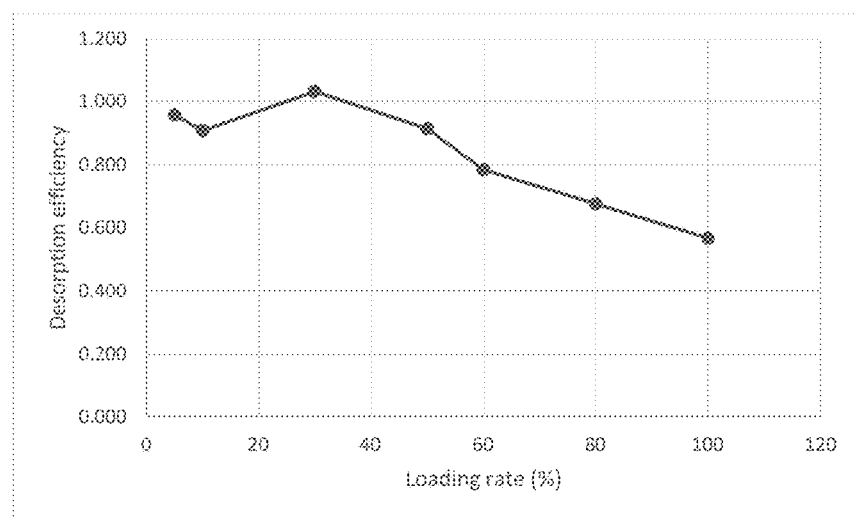
FIG. 22 shows the desorption efficiency using NaCl as desorbent agent as a function of resin loading rate (%), which was considered the amount of resin in grams present in 100 mL of desorbent.

Static desorption. A set of different resin concentrations (weight of resin/volume of desorbent) was tested. The resin loading rate (%) was considered the amount of resin in grams present in 100 mL of desorbent, e.g., 60% loading rate implies 60 g of resin per 100 mL of desorbent. Results in FIG. 21 show that an increase in resin loading rate correlates with an increase in final phytate concentration. Phytate-phosphorus is found at approximately 20 g $L^{-1}$ when a loading rate of 100% is applied and the system achieves chemical equilibrium. Desorption efficiency, shown in FIG. 22 has an optimum loading rate of 30%. Values above or below this range do not promote 100% desorption efficiency using NaCl as desorbent agent. The use of 30% loading rate was able to promote total desorption of phytate and a final concentration of 11.3 g $L^{-1}$ phytate-phosphorus solution.

Example 15

Conversion of Phytate to Inositol

Samples of calcium phytate were produced from thin stillage (TS) which was obtained from a dry milling ethanol plant located in the state of Iowa, USA. Sample 1 and 2 of calcium phytate were produced via anion exchange method with resin AG 1-X8 (140-1441/Bio-Rad, Berkeley, Calif.) and IRA-93 (15622/Polysciences Inc. Warrington, Pa.), respectively. Sample 3 was produced by precipitation method with calcium. Phosphorus kits (TNT 845/Hach, Loveland, Colo.) were used to measure the phosphorous (P). Phytin (calcium magnesium phytate) from Tokyo Chemical Industry Co. (Tokyo, Japan) was used as standard for inositol production. Inositol from Acroc Organics (Geel, Belgium) was used as standard for gas chromatography (GC) analysis. All chemicals used were in analytical grade.

Phosphorus profile analysis. Aliquots of samples of calcium phytate and phytin were dissolved with 2 M HCl to convert the undissolved phosphorus to a dissolved form. After centrifugation (7000 rpm for 5 min), total and reactive phosphorus in this phosphorus acid solution were respectively tested by phosphorus kits. Reactive phosphorus was regarded as phosphate phosphorus. Phytate phosphorus was calculated by subtracting the phosphate phosphorus from total phosphorus.

Acidic hydrolysis of phytate. Inositol productions were carried out by acidic hydrolysis of phytate in capped 15 mL glass vials. Vials were initially charged with 0.25 g of calcium phytate or phytin dissolved in 3 mL 2 M HCl and 3 mL polyethylene glycol (PEG) 400. The reaction mixture was heated to 150° C. for 4 h and then used for GC analysis. All hydrolysis experiments were performed in duplicates and the data are presented as the mean values for the replicates.

GC analysis for inositol. The hydrolysis reaction mixture was dried in a convection oven at 105° C. until a constant weight was obtained. After centrifugation (7000 rpm for 10 min), 6 mL ethanol was mixed with 2 mL of the supernatant to dissolve out inositol. The inositol was washed with 5 mL ethanol for 3 times, the ethanol was evaporated by keeping at 105° C. for 1 h. Then, 5 mL silylanization reagent (chlorotrimethylsilane, hexamethyldisilazane and dimethylformamide as 1:2:8 mixing in volume ratio, prepared before using) was added to dissolve the inositol. The solution was maintained at 70° C. for 10 min. After the reaction, 10 mL distilled water and 3 mL hexane were added to extract the inositol. Then the hexane layer was separated out for GC sample injection by centrifugation (7000 rpm for 5 min). The injection volume of this solution for the GC analysis was 1 μL. The analysis was carried out with a GC (Model 7820A/Agilent, Santa Clara, Calif.) using a HP-5 capillary column (30 m×0.32 mm×0.25 mm; Agilent, Santa Clara, Calif.). $H_2$ was used as the carrier gas. The column temperature was kept at 180° C. for 2 min, heated to 220° C. at 20° C./min, and maintained for 3 min. The temperatures of the injector and detector were set at 240° C. and 260° C., respectively.

Contents of total and phytate phosphorus in samples of calcium phytate. As shown in Table 2, commercial phytin has the highest contents of total and phytate phosphorus, and then followed with sample 1, 2 and 3 in sequence. That is most likely due to the completeness of phytate molecule in commercial phytin, which means most phytate in commercial phytin is inositol hexaphosphate (IP6). While the samples of phytate extracted from TS has already been partially degraded to inositol mono-, bis-, tris-, tetra-, and pentakisphosphates (IP1, IP2, IP3, IP4, and IP5, respectively) and inorganic phosphorus by the phytase secreted by yeast during the fermentation process in ethanol production. Therefore, for the same amount of samples, calcium phytate from TS has lower phytate phosphorus content. Since phytate molecule has more charged oxygen than phosphate molecule, anion exchange resins display a more powerful absorbability on phytate than phosphate. That is why phytate phosphorus contents in sample 1 and 2 are much higher than that in sample 3. For sample 3, phosphate precipitated out during the calcium precipitation for phytate, only 62.7% of phosphorus is phytate phosphorus.

TABLE 2

Phosphorus profile in samples of calcium phytate and phytin

| Sample No. | Total phosphorus/sample (mg/g) | Phytate phosphorus/sample (mg/g) | Phytate phosphorus/total phosphorus (%) |
|---|---|---|---|
| 1 | 168 | 157 | 93.1 |
| 2 | 157 | 118 | 75.5 |
| 3 | 151 | 94.6 | 62.7 |
| Phytin | 189 | 157 | 83.2 |

Figure 23:
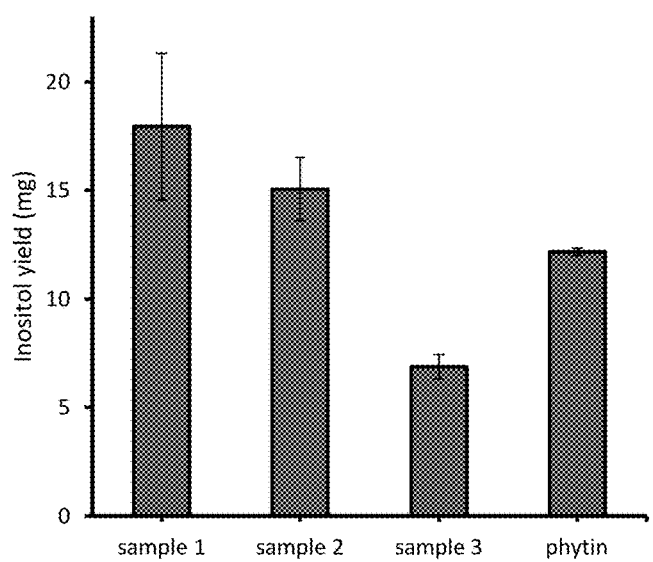
FIG. 23 shows inositol yield from the hydrolysis of phytate; reaction conditions were 0.25 g of samples dissolved with 3 mL of 2 M HCl, mixed with 3 mL PEG 400, heated to 150° C. for 4 h.

Inositol production from samples of calcium phytate and phytin. In order to avoid the side reaction, transesterification, which inositol is esterified with phosphate to re-form phytate, PEG 400 was added to compete with inositol in this side reaction. As shown in FIG. 23, the highest yield of inositol, 17.9 mg, was obtained from sample 1. Comparatively, 12.2 mg was produced from commercial phytin. We can reasonably deduce that the incomplete phytate molecule (like IP1, IP2, IP3, IP4, and IP5) has advantages to complete one (IP6) to get completely hydrolyzed. Thus, it is understandable to see higher yield of inositol was obtained from sample 2 than commercial phytin was based on lower phytate phosphorus content. As hydrolyzing phytate to inositol is a reversible reaction, high concentration of phosphate in reaction mixture will inhibit the proceeding of hydrolysis. That is why least inositol was detected in the reaction mixture of sample 3.

In the preceding description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

"Include," "including," or like terms means encompassing but not limited to, that is, including and not exclusive.

The present disclosure is illustrated by the following examples. It is to be understood that the particular examples, assumptions, modeling, and procedures are to be interpreted broadly in accordance with the scope and spirit of the disclosure as set forth herein.

Thus, embodiments of methods of extracting phytate from distillates are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A method for processing a distillate, the method comprising:
   contacting the distillate with an anion exchange resin, wherein the distillate comprises total phosphorus, wherein total phosphorus comprises soluble inorganic phosphorus, phytate phosphorus, other forms of phosphorus, or combinations thereof and wherein at least some of the soluble inorganic phosphorus, phytate phosphorus or both in the distillate is adsorbed on the anion exchange resin; and
   separating at least some of the distillate from the anion exchange resin to form a modified distillate, wherein the modified distillate has less total phosphorus than the distillate.

2. The method according to claim 1, wherein a combination of soluble inorganic phosphorus and phytate phosphorus are removed from the distillate to form the modified distillate.

3. The method according to claim 1, wherein the anion exchange resin is a basic anion exchange resin.

4. The method according to claim 1, wherein the step of separating at least some of the distillate from the anion exchange resin comprises removing the distillate from a container housing the anion exchange resin.

5. The method according to claim 1, wherein the steps of contacting and separating are continuous in that the method is part of a larger flow through system.

6. The method of claim 1 further comprising desorbing at least some of the soluble inorganic phosphorus, phytate phosphorus, or both from the anion exchange resin after at least some of the distillate has been contacted with the anion exchange resin.

7. The method of claim 6 further comprising separating phytate phosphorus from other forms of phosphorus.

8. The method of claim 6 further comprising regenerating the anion exchange resin after at least some of the soluble inorganic phosphorus, phytate phosphorus, or both have been desorbed from the anion exchange resin.

* * * * *